United States Patent
Chen et al.

(10) Patent No.: US 10,609,927 B2
(45) Date of Patent: Apr. 7, 2020

(54) REACTIVE ANTIBACTERIAL COMPOUND AND PREPARATION METHOD THEREOF

(71) Applicant: SHENZHEN UNIVERSITY, Guangdong (CN)

(72) Inventors: Shiguo Chen, Guangdong (CN); Lingjun Yuan, Guangdong (CN)

(73) Assignee: SHENZHEN UNIVERSITY, Shenzhen (CN)

( * ) Notice: Subject to any disclaimer, the term of this patent is extended or adjusted under 35 U.S.C. 154(b) by 0 days.

(21) Appl. No.: 16/232,392

(22) Filed: Dec. 26, 2018

(65) Prior Publication Data

US 2019/0133123 A1 May 9, 2019

Related U.S. Application Data

(60) Division of application No. 15/549,162, filed as application No. PCT/CN2015/090059 on Sep. 18, (Continued)

(51) Int. Cl.
| | |
|---|---|
| C07C 275/24 | (2006.01) |
| C07D 213/30 | (2006.01) |
| A01N 33/12 | (2006.01) |
| D06M 13/463 | (2006.01) |
| D06M 13/477 | (2006.01) |
| C07D 213/75 | (2006.01) |
| C07C 271/20 | (2006.01) |
| C07C 271/28 | (2006.01) |
| C07C 275/26 | (2006.01) |
| C07C 309/14 | (2006.01) |
| C07F 9/09 | (2006.01) |
| A01N 47/12 | (2006.01) |
| A01N 47/18 | (2006.01) |

(Continued)

(52) U.S. Cl.
CPC ............ *A01N 33/12* (2013.01); *A01N 27/00* (2013.01); *A01N 47/12* (2013.01); *A01N 47/18* (2013.01); *A01N 47/20* (2013.01); *A01N 47/28* (2013.01); *A01N 47/30* (2013.01); *A01N 57/12* (2013.01); *A01N 57/16* (2013.01); *C07C 211/62* (2013.01); *C07C 271/20* (2013.01); *C07C 271/28* (2013.01); *C07C 275/24* (2013.01); *C07C 275/26* (2013.01); *C07C 309/14* (2013.01); *C07D 213/30* (2013.01); *C07D 213/75* (2013.01); *C07F 9/091* (2013.01); *D06M 13/256* (2013.01); *D06M 13/292* (2013.01); *D06M 13/402* (2013.01); *D06M 13/432* (2013.01); *D06M 13/463* (2013.01); *D06M 13/467* (2013.01); *D06M 13/477* (2013.01); *D06M 16/00* (2013.01); *A01N 2300/00* (2013.01); *C07C 2601/14* (2017.05); *D06M 2400/01* (2013.01)

(58) Field of Classification Search
CPC .......................... C07C 275/24; C07D 271/20
See application file for complete search history.

(56) References Cited

U.S. PATENT DOCUMENTS

| | | |
|---|---|---|
| 2,982,862 A | 5/1961 | Smith |
| 6,828,029 B1 | 12/2004 | Lewis et al. |
| 2013/0273580 A1 | 10/2013 | Starcher et al. |
| 2014/0135408 A1 | 5/2014 | Wang et al. |

FOREIGN PATENT DOCUMENTS

| | | |
|---|---|---|
| CN | 101760963 A | 6/2010 |
| CN | 103361977 A | 10/2013 |

(Continued)

OTHER PUBLICATIONS

Jiang Yuan et al., Improvement of blood compatibility on cellulose membrane surface by grafting betaines, Colloids and Surfaces B: Biointerfaces, 30: 147-155 (2003).
Sang-Ho Ye et al., Nonthrombogenic, Biodegradable Elastomeric Polyurethanes with Variable Sulfobetaine Content, ACS Applied Materials & Interfaces, 6(24), 22796-22806 (2014).
International Search Report for PCT/CN2015/090059 dated Dec. 21, 2015, 7 pages.

(Continued)

*Primary Examiner* — Shawquia Jackson
(74) *Attorney, Agent, or Firm* — Metis IP LLC

(57) ABSTRACT

A reactive antibacterial compound is represented by the general formula (I):

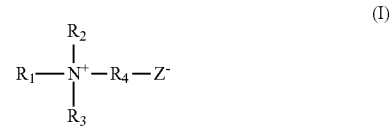

wherein $R_1$ represents OCN-L-NHCOOR', OCN-L-NHCONHR', OCN-L-NHCOSR', OCN-L-COOR', or OCN-L-COONHR'. G1 represents OCN-M-NHCOOG', OCN-M-NHCONHG', OCN-M-NHCOSG', OCN-M-COOG', or OCN-M-COONHG'. L, M, R' and G' independently for each occurrence represent divalent alkyl and cycloalkyl having from 1 to 18 carbon atoms, optionally substituted by up to 18 heteroatoms. $R_4$ and $G_4$ independently for each occurrence represent a divalent alkyl and cycloalkyl having from 1 to 18 carbon atoms, optionally substituted by at most 18 heteroatoms. $G_2$ and $G_3$ independently for each occurrence represent —H, —F, —Cl, —Br, —I, —OCH3, —OCH2CH3, —OPr, —CN, —SCN, —NO, —NO2, a monovalent unsubstituted or substituted alkyl, cycloalkyl, or aryl having from 1 to 7 carbon atoms. Z and X independently for each occurrence represent —COO, —SO3, or —OPO2OR$_5$. $R_5$ represents a monovalent unsubstituted or substituted alkyl, cycloalkyl, or aryl having from 1 to 6 carbon atoms.

20 Claims, No Drawings

Related U.S. Application Data 2015, now Pat. No. 10,368,544, which is a continuation of application No. PCT/CN2015/072439, filed on Feb. 6, 2015.

(51) Int. Cl.

| | | |
|---|---|---|
| *A01N 47/20* | (2006.01) | |
| *A01N 47/28* | (2006.01) | |
| *A01N 47/30* | (2006.01) | |
| *A01N 57/12* | (2006.01) | |
| *D06M 13/256* | (2006.01) | |
| *D06M 13/292* | (2006.01) | |
| *D06M 13/402* | (2006.01) | |
| *D06M 13/432* | (2006.01) | |
| *D06M 13/467* | (2006.01) | |
| *D06M 16/00* | (2006.01) | |
| *A01N 27/00* | (2006.01) | |
| *A01N 57/16* | (2006.01) | |
| *C07C 211/62* | (2006.01) | |

(56) References Cited

FOREIGN PATENT DOCUMENTS

| JP | 2012031400 A | 2/2012 |
|---|---|---|
| JP | 2012048224 A | 3/2012 |
| JP | 2013234157 A | 11/2013 |

OTHER PUBLICATIONS

Written Opinion of the International Search Authority for PCT/CN2015/090059 dated Dec. 21, 2015, 11 pages.
International Search Report for PCT/CN2015/072439 dated Oct. 28, 2015, 6 pages.
Written Opinion of the International Search Authority for PCT/CN2015/072439 dated Oct. 28, 2015, 12 pages.
Jiang Yuan et al, Construction of Sulfoammonium Zwitterionic Structure onto Surface of Polyurethane by Hexamethylene Diisocyanate (HDI) Spacer for Improving Blood Compatibility, Chemical Journal of Chinese Universities, 24(5), 916-919 (2003).
Mi, et al, Angew. Chem. Int. Ed., 2014, 53, 1746-1754.

REACTIVE ANTIBACTERIAL COMPOUND AND PREPARATION METHOD THEREOF

CROSS-REFERENCE TO RELATED APPLICATIONS

The present application is a Divisional of U.S. Utility patent application Ser. No. 15/549,162 entitled "REACTIVE ANTIBACTERIAL COMPOUND AND PREPARATION METHOD THEREOF," filed on Aug. 6, 2017 which is a U.S. national stage of International Application No. PCT/CN2015/090059, filed on Sep. 18, 2015 which claims priority of PCT Application No. PCT/CN2015/072439 filed on Feb. 6, 2015. Each of the above applications are incorporated herein by reference in their entireties.

TECHNICAL FIELD

The present application generally relates to the field of antibacterial technologies, particularly to a reactive antibacterial compound and a preparation method thereof, and more particularly to a reactive antibacterial compound with positively charged nitrogen atoms and a preparation method thereof.

BACKGROUND

Bacterial and fungal infections have become a worldwide problem that threatens human health and is highly concerned in the global health care industry. One of the important means to solve the problem of bacterial or fungal infections is to impart antibacterial properties to the surface of a material or a product, so as to prevent bacteria or fungi from growing or proliferating on the surface of the material or the product, or even to kill the bacteria or fungi already present on the surface. The usual solution is to adhere or anchor antibacterial components or materials to the surface of the product by means of spray coating and/or chemical bonding, thereby achieving the antibacterial properties. Known antibacterial materials are widely applied on ceramics, glass products, plastics, rubbers, fibers, papers, painting, etc., such as household appliances, furniture, janitorial supplies, food packages, and clothing. At present, world-wide antibacterial materials may be classified into four categories: (1) inorganic antibacterial agents, such as nano-titanium dioxide, nano-silver, nano-copper, and ions thereof; (2) organic antibacterial agents, such as quaternary ammonium salts, alcohols, haloamines, biguanides, and thiazoles; (3) polymeric antibacterial agents, such as polymeric quaternary ammonium salts; and (4) natural and modified antibacterial agents, such as chitosans and sorbic acids.

In order to impart antibacterial properties to the surface of the material or product, the most common method is to cover the surface with a coating containing antibacterial agents (such as nano-silver, nano-copper, and ions thereof, or other antibacterial agents), and/or nano-silver, nano-copper, silver ions, copper ions, other heavy metals. Relying on the slow release of metal ions into the ambient environmental, the purpose of bacteriostasis or sterilization is thereby achieved. However, the antibacterial capability of these metal ions gradually reduces over time until the antibacterial capability is completely lost, meanwhile, microorganisms may be induced to mutate by the metal ions, thus increasing the probability that the microorganisms develop drug resistance. In addition, harmfulness of nano-materials has gradually been recognized and paid attention by human beings.

The organic antibacterial compounds, such as quaternary ammonium salts, alcohols, haloamines, biguanides, and thiazoles, bear the characteristics of taking effect in short time, and extinguishing bacterias efficiently. This category of antibacterial agents mainly includes quaternary ammonium salts and quaternary phosphonium salts. Generally, cell walls of bacteria are negatively charged, and ions, such as quaternary ammonium salts and the quaternary phosphonium salts, are positively charged. The quaternary ammonium salts with positive charges are liable to be absorbed by the bacteria, penetrating the cell walls after approaching the bacteria, being bonded to the cytomembrane, and disrupting the composition of the cytomembrane, which results in leaking of intracellular materials and eventually death of the bacteria. However, the chemical activeness of the quaternary ammonium salts, which exist substantially in a free state during use and have high toxicity and strong irritation, is low. When used as antibacterial agents, the quaternary ammonium salts have poor heat resistance, tend to migrate and can be washed easily. Moreover, the quaternary ammonium salts tend to enrich on skins of human bodies gradually, thus a long-term use of quaternary ammonium salts may cause microorganisms to mutate, resulting in drug resistance for these microorganisms. Meanwhile, the organic antibacterial agents have poor heat resistance, thereby limiting their use range thereof.

The polymeric quaternary ammonium salt antibacterial agents can overcome problems of micro-molecule antibacterial agents, such as being volatile, unworkable, chemically unstable. Moreover, the polymeric quaternary ammonium salt antibacterial agents exhibit good antibacterial activeness, and are less permeating, which helps drawing attention of the people. At present, however, the unimmobilized polymeric antibacterial agents also exhibit drawbacks such as high leachability and lack of sustainability, which presents pressure to the ambient environment as well.

The natural antibacterial agents are derived from extracts of natural plants, animals or minerals, whose main antibacterial mechanism is similar to that of the organic quaternary ammonium salts, but are less effective than the organic antibacterial agents, and products of the natural antibacterial agents are not yet mature. Another drawback of the natural antibacterial agents is that they are not suitable for mass production, so that their application thereof is limited.

Therefore, there is a need to develop and prepare antibacterial agents which are green, immobilizable, and durable.

SUMMARY

According to some embodiments of the present disclosure, a reactive antibacterial compound is provided, which exhibits excellent antibacterial property and behaves as hydrophilic, and can react with and bind to functional groups on surfaces of natural fibers, synthetic fibers and polymeric materials by a terminal isocyanate, thereby achieving durable antibacterial effects. The terminal isocyanate may refer to an isocyanate at the end of a molecular chain.

In some embodiments, the antibacterial compound is a zwitterionic compound having a terminal isocyanate and a quaternary ammonium group. The positive charge of a quaternary nitrogen atom may damage cytomembrane of microorganisms, thereby denaturing protein and damaging cell structures. The microorganisms may include but not limited to E. coli, S. typhimurium, P. aeruginosa, S. aureas, C. albicans, sulfate reducing bacteria, Gram-positive bacteria, Gram-negative bacteria, S. epidermidis, E. faecalis, C.

xerosis, B. anthracis, etc. The antibacterial compound may be used as a sterilizing agent or a bacteriostatic agent to prevent infections, terminate microorganisms or inhibit physiological functions of the microorganisms, and thus treating effectively the infections caused by these microorganisms, or confining pollution caused by the same.

In some embodiments, the antibacterial compound may be chemically bound to the surface of materials through a terminal isocyanate. The antibacterial compound may be applied to textile, medicine, food, and agriculture fields, but not limited thereto. For example, the isocyanate may be bound to a hydroxyl or amino on surface of a fiber, a cotton textile, or a nylon, to produce an antibacterial textile with detergent resistance; may be bound to a hydroxyl or amino on surface of a medical perfusion tube or packaging material, to produce an antibacterial medical product; or may be bound to a hydroxyl or amino on the surface of a food package or food preservation material, to produce an antibacterial packaging material.

According to an aspect of the present disclosure, the antibacterial compound may be represented by the general formula (I):

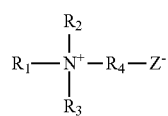
(I)

wherein, $R_1$ represents OCN-L-NHCOOR', OCN-L-NHCONHR', OCN-L-NHCOSR', OCN-L-COOR', or OCN-L-COONHR';

L represents a divalent unsubstituted or substituted alkyl, cycloalkyl, or aryl having from 1 to 18 carbon atoms, optionally substituted by at most 18 heteroatoms;

R' represents a divalent unsubstituted or substituted alkyl, cycloalkyl, or aryl having from 1 to 18 carbon atoms, optionally substituted by at most 18 heteroatoms;

$R_2$ and $R_3$ independently for each occurrence represent a monovalent unsubstituted or substituted alkyl, cycloalkyl, or aryl having from 1 to 18 carbon atoms, optionally substituted by at most 18 heteroatoms;

$R_4$ independently represents a divalent unsubstituted or substituted alkyl, cycloalkyl, or aryl having from 1 to 18 carbon atoms, optionally substituted by at most 18 heteroatoms;

Z represents —COO, —$SO_3$, or —$OPO_2OR_5$; and wherein, $R_5$ represents a monovalent unsubstituted or substituted alkyl, cycloalkyl, or aryl having from 1 to 6 carbon atoms.

In some embodiments, in the antibacterial compound, the $R_2$ and $R_3$ are the same or different groups.

In some embodiments, in the antibacterial compound, the $R_2$ and the $R_3$ independently for each occurrence represent —$(CH_2)_u CH_3$, and u is an integer within a range from 0 to 17. Preferably, u is 0, 1, 2, 3, 4, 5, 6, 7, 8, 9, 10, 11, 12, 13, 14, 15, 16, or 17; further more preferably, u is 0, 1, 2, 3, or 4; more preferably, u is 0, 1, or 2.

In some embodiments, in the antibacterial compound, the Z represents —$SO_3$.

In some embodiments, in the antibacterial compound, the Z represents —$CO_2$.

In some embodiments, in the antibacterial compound, the Z represents —$OPO_2OR_5$.

In some embodiments, in the antibacterial compound, the $R_5$ represents —$(CH_2)wCH_3$, and w is an integer within a range from 0 to 5.

In some embodiments, in the antibacterial compound, the $R_4$ and the R' independently for each occurrence represent —$(CH_2)_n$—, and n is an integer within a range from 1 to 18. Preferably, n is 1, 2, 3, 4, 5, 6, 7, 8, 9, 10, 11, 12, 13, 14, 15, 16, 17, or 18; more preferably, n is 1, 2, 3, 4, 5, 6, 7, 8, 9, or 10; further more preferably, n is 0, 1, 2, 3, 4, 5, 6, or 7.

In some embodiments, in the antibacterial compound, the $R_1$ represents OCN-L-NHCOOR' or OCN-L-NHCONHR'.

In some embodiments, in the antibacterial compound, the L represents:

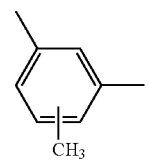

According to another aspect of the present disclosure, the antibacterial compound are represented by the general formula (II):

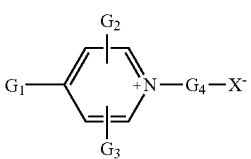
(II)

wherein, $G_1$ represents OCN-M-NHCOOG', OCN-M-NHCONHG', OCN-M-NHCOSG', OCN-M-COOG', or OCN-M-COONHG';

M represents a divalent unsubstituted or substituted alkyl, cycloalkyl, or aryl having from 1 to 18 carbon atoms;

G' represents a divalent unsubstituted or substituted alkyl, cycloalkyl, or aryl having from 1 to 18 carbon atoms;

$G_2$ and $G_3$ independently for each occurrence represent —H, —F, —Cl, —Br, —I, —$OCH_3$, —$OCH_2CH_3$, —OPr, —CN, —SCN, —NO, —$NO_2$, a monovalent unsubstituted or substituted alkyl, cycloalkyl, or aryl having from 1 to 7 carbon atoms;

$G_4$ represents a divalent unsubstituted or substituted alkyl, cycloalkyl, or aryl having from 1 to 18 carbon atoms;

X represents —COO, —$SO_3$, or —$OPO_2OR_5$; and $R_5$ represents a monovalent unsubstituted or substituted alkyl, cycloalkyl, or aryl having from 1 to 6 carbon atoms.

In some embodiments, in the antibacterial compound, the $G_1$ represents OCN-M-NHCOOG' or OCN-M-NHCONHG'.

In some embodiments, in the antibacterial compound, the $G_2$ and $G_3$ are the same or different groups.

In some embodiments, in the antibacterial compound, the $G_2$ and $G_3$ independently for each occurrence represent —H, —$CH_3$, —$CH_2CH_3$, —$NO_2$, —F, —Cl, —Br, or —I.

In some embodiments, in the antibacterial compound, the X represents —$SO_3$.

In some embodiments, in the antibacterial compound, the X represents —$CO_2$.

In some embodiments, in the antibacterial compound, the X represents —$OPO_2OR_5$.

In some embodiments, in the antibacterial compound, the $R_5$ represents —$(CH_2)_wCH_3$, and w is an integer within a range from 0 to 5. Preferably, w is 0, 1, 2, 3, or 4, more preferably, w is 0, 1, or 2.

In some embodiments, in the antibacterial compound, the $G_4$ and the G' independently for each occurrence represent —$(CH_2)_n$—, and n is an integer within a range from 1 to 18. Preferably, n is 1, 2, 3, 4, 5, 6, 7, 8, 9, 10, 11, 12, 13, 14, 15, 16, 17, or 18; more preferably, n is 1, 2, 3, 4, 5, 6, 7, 8, 9, or 10; further more preferably, n is 0, 1, 2, 3, 4, 5, 6, or 7.

In some embodiments, in the antibacterial compound, the M represents:

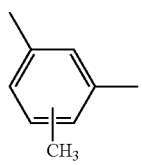

According to another aspect of the present disclosure, a preparation method for an antibacterial compound include:

reacting tertiary amine represented by the general formula (III) with a reactant B represented by the general formula (IV), and generating a mixture;

wherein: the Y represents —OH, —$NH_2$, or —SH; R' represents a divalent unsubstituted or substituted alkyl, cycloalkyl, or aryl having from 1 to 18 carbon atoms; $R_2$ and $R_3$ independently for each occurrence represent a monovalent unsubstituted or substituted alkyl, cycloalkyl, or aryl having from 1 to 18 carbon atoms; L represents a divalent unsubstituted or substituted alkyl, cycloalkyl, or aryl having from 1 to 18 carbon atoms; and D represents —COOH or —NCO;

reacting the mixture with a reactant A, and generating the antibacterial compound;

wherein: the reactant A represents propane sultone, butane sultone, β-propiolactone, $X(CH_2)_vCO_2$—$Mt^+$, $X(CH_2)_vSO_3$—$Mt^+$, or cyclic phosphate ester, the X represents Br, Cl, or I, v is an integer greater than 0, $Mt^+$ represents $Li^+$, $Na^+$, $K^+$, $NH_4^+$, $Ag^+$, $½Mg^{2+}$, or $½Ca^{2+}$, and the cyclic phosphate ester represents:

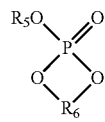

wherein: $R_5$ represents a monovalent unsubstituted or substituted alkyl, cycloalkyl, or aryl having from 1 to 6 carbon atoms; and $R_6$ represents a divalent unsubstituted or substituted alkyl having from 1 to 6 carbon atoms.

In some embodiments, in the preparation method for the antibacterial compound, the tertiary amine and the reactant B are reacting in the presence of catalyst C, and the catalyst C represents at least one of organic amine, a phosphorus compound, or a metal-containing catalyst.

In some embodiments, in the preparation method for the antibacterial compound, the catalyst C represents the metal-containing catalyst.

In some embodiments, in the preparation method for the antibacterial compound, the metal-containing catalyst represents tin tetrachloride, tetrabutyl tin, tributyl tin chloride, dibutyl tin dichloride, butyl tin trichloride, tributyl tin cyanide, dibutyl tin diacetate, dibutyl tin dioctoate, tributyl tin octoate, diphenyl tin dioctoate, dibutyl tin dibutoxy, dibutyl tin bis(acetylacetoate), dibutyl tin bis(isooctylmaleate), dioctoate tin oxide, dibutyl tin sulfide, stannous oleate, stannous tartrate, dibutyl tin dilaurate, stannous octoate, or metal naphthenate.

In some embodiments, in the preparation method for the antibacterial compound, the catalyst C represents the metal naphthenate.

In some embodiments, in the preparation method for the antibacterial compound, the metal naphthenate represents at least one of copper naphthenate, zinc naphthenate, lead naphthenate, lithium naphthenate, cobalt naphthenate, nickel naphthenate, cadmium naphthenate, mercury naphthenate, indium naphthenate, or bismuth naphthenate.

According to another aspect of the present disclosure, a preparation method for an antibacterial compound include:

1) reacting pyridine represented by the general formula (V) with a reactant B represented by the general formula (IV), and generating a mixture;

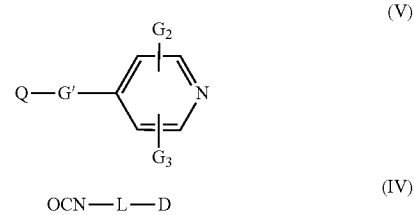

wherein: the Q represents —OH, —$NH_2$, or —SH; G' represents a divalent unsubstituted or substituted alkyl, cycloalkyl, or aryl having from 1 to 18 carbon atoms; $G_2$ and $G_3$ independently for each occurrence represent —H, —F, —Cl, —Br, —I, —$OCH_3$, —$OCH_2CH_3$, —OPr, —CN, —SCN, —NO, —$NO_2$, a monovalent unsubstituted or substituted alkyl, cycloalkyl, or aryl having from 1 to 7 carbon atoms; D represents —COOH or —NCO; and L represents a divalent unsubstituted or substituted alkyl, cycloalkyl, or aryl having from 1 to 18 carbon atoms.

2) reacting the mixture with a reactant A, and generating the antibacterial compound;

wherein: the reactant A represents propane sultone, butane sultone, 3-propiolactone, $X(CH_2)_vCO_2$—$Mt^+$, $X(CH_2)_vSO_3$—$Mt^+$, or cyclic phosphate ester, the X represents Br, Cl, or I, v is an integer greater than 0, $Mt^+$ represents $Li^+$, $Na^+$, $K^+$, $NH_4^+$, $Ag^+$, $½Mg^{2+}$, or $½Ca^{2+}$, and the cyclic phosphate ester represents:

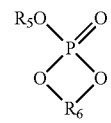

wherein: $R_5$ represents a monovalent unsubstituted or substituted alkyl, cycloalkyl, or aryl having from 1 to 6 carbon atoms; and $R_6$ represents a divalent unsubstituted or substituted alkyl having from 1 to 6 carbon atoms.

In some embodiments, in the preparation method for the antibacterial compound, the pyridine and the reactant B are reacting in the presence of catalyst C, and the catalyst C represents at least one of organic amine, a phosphorus compound, or a metal-containing catalyst.

In some embodiments, in the preparation method for the antibacterial compound, the catalyst C represents the metal-containing catalyst.

In some embodiments, in the preparation method for the antibacterial compound, the metal-containing catalyst represents tin tetrachloride, tetrabutyl tin, tributyl tin chloride, dibutyl tin dichloride, butyl tin trichloride, tributyl tin cyanide, dibutyl tin diacetate, dibutyl tin dioctoate, tributyl tin octoate, diphenyl tin dioctoate, dibutyl tin dibutoxy, dibutyl tin bis(acetylacetoate), dibutyl tin bis(isooctylmaleate), dioctoate tin oxide, dibutyl tin sulfide, stannous oleate, stannous tartrate, dibutyl tin dilaurate, stannous octoate, or metal naphthenate.

In some embodiments, in the preparation method for the antibacterial compound, the catalyst C represents the metal naphthenate.

In some embodiments, in the preparation method for the antibacterial compound, the metal naphthenate represents at least one of copper naphthenate, zinc naphthenate, lead naphthenate, lithium naphthenate, cobalt naphthenate, nickel naphthenate, cadmium naphthenate, mercury naphthenate, indium naphthenate, or bismuth naphthenate.

DETAILED DESCRIPTION

The following description is presented with a combination of specific embodiments, and it should be noted that descriptions and embodiments given herein are merely for the purposes of describing the specific embodiments of the present disclosure, to make features of the embodiments of the present disclosure more readily understood, and are not intended to be limiting the scope of the claims.

Unless otherwise specified, the term "aliphatic", "alicyclic", and "aromatic" in the present disclosure include but not limited to linear, branched, or cyclic groups, being unsubstituted, substituted by one or more heteroatoms, or substituted by one or more groups having a heteroatom. Wherein, "aliphatic" and "alicyclic" groups may be saturated or unsaturated, such as an olefine, a cycloolefine, a diolefin, a cyclodiolefin, an alkyne, a cycloalkyne, and a polycyclic hydrocarbon. Aromatic groups may refer to a system having at least one aromatic ring, i.e., a pure aromatic compound such as benzene, naphthalene and anthracene, or an aromatic compound having an aliphatic group, such as toluene, styrene and phenylethyne. The pure aromatic compound, having a monocycle aromatic compound and a fused ring aromatic compound, may be an aromatic hydrocarbon, such as benzene, naphthalene, and anthracene, or may be an aromatic system having heteroatoms, such as pyridine, furan, and thiophene.

The heteroatom or the group having a heteroatom may include but not limited to a halogen (—F, —Cl, —Br, —I), hydroxyl (—OH), carboxyl (—COOH), acyl (—CO—), acyloxy (—COO—), amino (—NH$_2$), alkylamino (—NHR), dialkylamino (—NR$_1$R$_2$), arylamino (—NHAr), amide (—CONH$_2$), ester (—COOR), carboxamide (—CONR$_1$R$_2$), carbamate (—NHCOOR), alkoxyl (—OR), aryloxy (—OAr), alkylthio (—SR), arylthio (—SAr), alkyl sulfonate (—OSO$_2$R), nitro (—NO$_2$), cyano (—CN), isocyano (—NC), oxo (=O), azo (—N=N—), thiol (—SH), sulfonyl (—SO$_2$R), phosphono (—PO(OR$_1$)(OR$_2$)), phosphinyl)

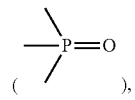

a thioester (—NCS), thioalkoxy (—OCSR), thiocyanate (—SCN), isothiocyanate (—NCS), a phosphate ester or salt (—OP(O)(OH)$_2$), a sulfate ester or salt (—OSO$_2$(OH)), or a combination thereof.

Herein, an alkyl, cycloalkyl, and aryl should be explained as below. As appreciated by those skilled in the art, the alkyl may refer to a saturated hydrocarbon group which is formed by removing a hydrogen atom from an alkane molecule, such as methyl, methylene, ethyl, or isopropyl; the cycloalkyl may refer to the general term for hydrocarbon groups formed by a removal of a hydrogen atom from a saturated hydrocarbon having an alicyclic structure, for example, a monocyclic alicyclic hydrocarbon and a fused ring alicyclic hydrocarbon, such as cyclobutyl or cyclopentyl; the aryl may refer to the general term of groups formed by removing a hydrogen atom from an aromatic nucleus or other carbon atom of any aromatic hydrocarbon molecules, such as phenyl, o-tolyl, 1-naphthyl (or α-naphthyl), 2-naphthyl (or β-naphthyl), benzyl, or phenylethyl.

A monovalent hydrocarbon group may refer to a group formed by a removal of a hydrogen atom in hydrocarbons, such as methyl (—CH$_3$), ethyl (—CH$_2$CH$_3$), phenyl (—C$_6$H$_5$); a bivalent hydrocarbon group may refer to a group formed by a removal of two hydrogen atoms in hydrocarbons, such as methylene (—CH$_2$—), ethylidene (—CH$_2$CH$_2$—), or p-phenylene (-p-C$_6$H$_4$—). Similarly, valences of other functional groups also have the same meaning, for example, nitro is monovalent (—NO$_2$), and oxo is divalent (=O).

According to some embodiments of the present disclosure, the structural framework of the antibacterial compound may include a quaternary ammonium group with a positive charge, the group having a good antibacterial property, and in order to make the whole compound electrically neutral, the structure of the antibacterial compound may also include a group with a negative charge, the group being attached to the main framework. In addition, the compound may further include an isocyanate group at the end of the molecule, and the compound may be bound to materials such as polymeric fibers and natural fibers by reacting the isocyanate group with a functional group in the materials.

According to one aspect of the present disclosure, a preparation method for the antibacterial compound may include the following steps:

React tertiary amine represented by the general formula (III) with a reactant B represented by the general formula (IV), and generate a mixture;

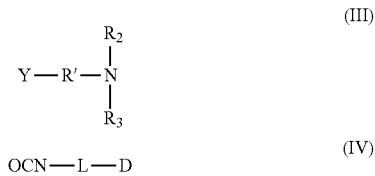

wherein, the Y represents —OH, —NH$_2$, or —SH; R' represents a divalent alkyl, cycloalkyl, or aryl having from 1 to 18 carbon atoms, optionally substituted by at most 18 heteroatoms; $R_2$ and $R_3$ independently for each occurrence represent a monovalent unsubstituted or substituted alkyl, cycloalkyl, or aryl having from 1 to 18 carbon atoms; L represents a divalent unsubstituted or substituted alkyl, cycloalkyl, or aryl having from 1 to 18 carbon atoms; and D represents —COOH or —NCO.

In this reaction, a typical nucleophilic addition reaction may occur between the functional group Y (—OH, —SH, or —NH$_2$) in the tertiary amine represented by the general formula (III) and the isocyanate functional group (—NCO) in the reactant B represented by the general formula (IV), and generate a carbamate, thiocarbamate or urea structure. The reactant B may include an isocyanate functional group and another isocyanate functional group or carboxyl group (functional group D). In the first step of the reaction, the isocyanate functional group in the compound represented by the general formula (III) may react with the functional group Y in the compound represented by the general formula (IV), and the functional group D is reserved at one end.

It should be understood that a similar antibacterial compound having a terminal isocyanate can be obtained via the above reaction through any compound having at least two isocyanates. Since a polyisocyanate compound may include a plurality of isocyanates, only one of the plurality of isocyanates in a molecule is reacted, and other isocyanates are reserved in the final antibacterial compound when a nucleophile is not excessive. The number of carbon atoms or the molecular weight of the polyisocyanate compound has no effect on the reaction, as long as a nucleophilic addition reaction can occur between the polyisocyanate compound and the nucleophile. The polyisocyanate may be a aliphatic polyisocyanate, an alicyclic polyisocyanate, a heterochain polyisocyanate, an aromatic polyisocyanate, a substituted aliphatic or alicyclic or heterocyclic polyisocyanate, wherein the substituent may include but not limited to —F, —Cl, —Br, —I, —OCH$_3$, —OCH$_2$CH$_3$, —OPr, —CN, —SCN, —NO, —NO$_2$, etc. As is well known to those skilled in the art, the polyisocyanate compound may often present in a form of a dimer, a trimer, or other polymers, accordingly, the polyisocyanate herein may also include a monomer, a dimer, a trimer or other oligomers thereof.

The aliphatic polyisocyanate may include but not limited to hexamethylene diisocyanate, tetramethylene diisocyanate, 1,8-octamethylene diisocyanate, 1,10-decamethylene diisocyanate, 1,12-dodecamethylene diisocyanate, 1,14-tetradecylmethylene diisocyanate, a derivative of lysine diisocyanate, trimethylhexane diisocyanate, tetramethylhexane diisocyanate, and a dimer, a trimer, and other oligomers thereof.

The alicyclic or heterocyclic polyisocyanate may include but not limited to 1,4-, 1,3- or 1,2-diisocyanate cyclohexane, 4,4- or 2,4-di(isocyanate cyclohexyl)methane, 1-isocyanate-3,3,5-trimethyl-5-(isocyanatemethyl)cyclohexane(isophorone diisocyanate), 1,3- or 1,4-di(isocyanatemethyl)cyclohexane, 2,4- or 2,6-diisocyanate-1-methylcyclohexane, a 3(or 4),8(or 9)-di(isocyanate methyl)tricyclo[5.2.1.0.2.6]decane isomer mixture, norborene diisocyanate, 4,5-di(isocyanatomethyl)-1,3-dithiolane, and a dimer, a trimer, and other oligomers thereof.

The heterochain polyisocyanate may include but not limited to di(isocyanatomethylthio)methane, di(isocyanatomethylthio)methylthio methane, di(2-isocyanatoethylthio)methane, di(3-isocyanatopropylthio)methane, di(isocyanato methylthio)phenyl methane, di(2-isocyanatoethylthio)phenyl methane, di(3-isocyanatopropylthio)phenyl methane, 1,2-(diisocyanatoethylthio)ethane, 1-isocyanatomethylthio-2-(2-isocyanatoethylthio)ethane, 1-isocyanatoethylthio-2-(3-isocyanatopropylthio)ethane, di(isocyanatomethylthioethyl) sulfoether, tetra(isocyanatomethylthio)-1,4-dithiane, 2,2,5,5-tetra(isocyanatomethylthio)-1,3-dithiane, tri(isocyanato methylthio)methane, and a dimer, a trimer, and other oligomers thereof.

The aromatic polyisocyanate may include but not limited to toluene diisocynate, diphenylmethane diisocyanate, o-xylene diisocyanate, m-xylene diisocyanate, p-xylene diisocyanate, α,α,α',α'-tetramethyl-p-xylene diisocyanate, 1,3,5-tri(isocyanatomethyl)benzene, 4-methyl m-xylene diisocyanate, 4-ethyl m-xylene diisocyanate, 1,5-naphthalene diisocyanate, and a dimer, a trimer, and other oligomers thereof; 4-chloro m-xylene diisocyanate, 4,5-dichloro m-xylene diisocyanate, 2,3,5,6-tetrabromo p-xylene diisocyanate, and a dimer, a trimer, and other oligomers thereof.

In some embodiments, the isocyanate structure may also be a terminal isocyanate organic compound having at least one carboxyl (—COOH), a backbone structure of the organic compound may include an unsubstituted or substituted aliphatic, alicyclic, heterochain, heterocyclic, aromatic structure, wherein the substituent may include but not limited to —F, —Cl, —Br, —I, —OCH$_3$, —OCH$_2$CH$_3$, —OPr, —CN, —SCN, —NO, —NO$_2$, etc.

Taking a reaction of dimethyl ethanolamine and tetramethylene diisocyanate as an example, when the two reactants react in a molar ratio of 1:1, the reaction formula is as follows:

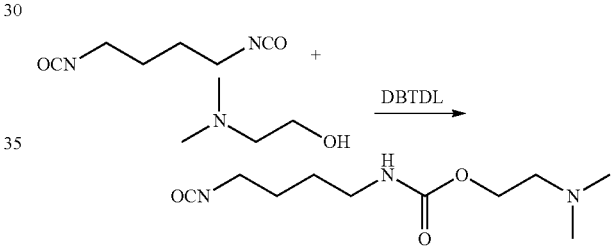

As for the amine used in the first step of the reaction, tertiary amine having a highly nucleophilic group Y, such as a hydroxyl, a thiol, or an amino (—NH$_2$), may be needed. Wherein, the function of the group Y is to attack the carbon atom of the isocyanate through lone pair electrons carried by oxygen, sulfur, and nitrogen atoms, so as to couple with the isocyanate. Since the amine compound may also couple with the isocyanate through a nitrogen atom, which may compete with the group Y in reacting with the isocyanate, so that tertiary amine with lower reactive activity is needed here. With a larger steric hindrance, the nitrogen atom in the tertiary amine may be more difficult to couple with the isocyanate.

Exemplary tertiary amine having a nucleophilic group may include but not limited to N,N-dimethyl ethanolamine, N,N-diethyl ethanolamine, N,N-dimethyl ethylenediamine, N,N-di-n-propyl ethanolamine, N,N-diisopropyl ethanolamine, N,N-di-n-butyl ethanolamine, N,N-di-n-pentyl ethanolamine, N,N-dicyclohexyl ethanolamine, dimethylamino methanthiol, dimethylamino ethanethiol, or 3,3'-iminobis(N,N-dimethyl propylamine).

In the presence of an alkaline reagent (such as tertiary amine, phosphines), the hydrogen atom in the Y functional group may also be removed in the form of a hydrogen ion, the nucleophilicity of O, S, and N atoms in the Y functional group may further be improved, so that the alkaline reagent may be used as a catalyst. While, in the presence of a Lewis acid such as a metal ion and an organometallic compound, the oxygen atom in the isocyanate may form a coordination bond with the Lewis acid, a part of electrons are transferred onto the metal atom from the oxygen atom, so that the electropositivity of the carbon atom in the isocyanate may be further enhanced, which facilitates receiving an attack from the nucleophile, and thus the Lewis acid may be used as a catalyst.

In a preparation using a catalyst, preferably, the catalyst may be one, two, or a combination of an organic amine compound, a phosphorus compound, and a metal-containing catalyst.

The organic amine compound may be classified to several categories: aliphatic amines, such as N,N-dimethyl cyclohexane, bis(2-dimethylamino ethyl)ether, N,N,N',N'-tetramethyl alkylene diamine, triethylamine, or N,N-dimethyl benzylamine; alicyclic amines, such as triethylene diamine (DABCO), N-ethyl morpholine, N-methyl morpholine, N,N'-diethyl piperazine, or dimethylamino cyclohexane; and aromatic amines, such as N,N-dimethyl aniline, pyridin, or 4-dimethylamino pyridine (N,N-dimethyl pyridine). A common property of the amine compounds may include that they are all alkaline and may accelerate the reaction. Meanwhile, the amine compounds all include a tertiary nitrogen atom or a pyridine nitrogen atom, and thus cannot react with the isocyanate.

Similar to the amine compounds, the phosphorus compounds may also function as an alkaline and accelerate the reaction. The phosphorus compounds may include but not limited to various tertiary phosphines in which three organic groups substituting three hydrogen atoms may be completely the same or completely different. Tertiary phosphines substituted by three same organic groups may include but not limited to triphenyl phosphine, trimethyl phosphine, triethyl phosphine, tri-n-propyl phosphine, triisopropyl phosphine, tri-n-butyl phosphine, or tri-t-butyl phosphine. Tertiary phosphines substituted by three different organic groups may include but not limited to dimethyl phenyl phosphine, methyl diphenyl phosphine, diethyl phenyl phosphine, or ethyl diphenyl phosphine.

In the metal-containing catalyst, since the metal ion may generally bind to the oxygen atom in the isocyanate to form a complex, electrons in the oxygen atom may transfer onto the metal atom, which enhances the electropositivity of the carbon atom bound thereto, facilitating the carbon atom receiving an attack from the nucleophile. The metal-containing catalyst may include but not limited to an inorganic metal salt, carboxylate, phenolate, metal alkylates, wherein carboxylate may be classified to linear or branched carboxylate and cyclic naphthenate. The metal elements contained are mainly alkali metals (lithium, sodium, potassium, rubidium, cesium, etc.); alkali earth metals (magnesium, calcium, strontium, barium); transition metals (uranium, cerium, titanium, zirconium, vanadium, chromium, molybdenum, manganese, ferrum, cobalt, nickel, copper, zinc, cadmium, mercury, etc.), aluminum, gallium, indium, thallium, tin, plumbum, stibium, bismuth, etc., but not limited thereto.

Common metal-containing catalysts may include but not limited to lithium acetate, lithium octanoate, lithium naphthenate, sodium trichlorphenate, sodium stearate, potassium acetate, potassium octanoate, calcium acetate, calcium octanoate, strontium naphthenate, barium acetate, uranyl nitrate, cerium nitrate, titanium tetrachloride, dibutyl titanium dichloride, titanium tetrabutyl, butoxy titanium trichloride, zirconium naphthenate, zirconium octanoate, vanadium trichloride, chromium naphthenate, molybdenum hexacarbonyl, manganese octanoate, ferric trichloride, ferrum octanoate, ferrum triacetylacetonate, ferrocene, cobalt octanoate, cobalt naphthenate, cobalt linoleate, cobalt benzoate, nickelocene, nickel octanoate, nickel naphthenate, copper acetate, copper octanoate, copper naphthenate, zinc octanoate, zinc naphthenate, cadmium nitrate, cadmium naphthenate, mercury diphenyl, mercury naphthenate, aluminum triphenyl, aluminium stearate, gallium acetate, indium naphthenate, thallium octanoate, tin tetrachloride, tin tetrachloride, etrabutyl tin, tributyl tin chloride, dibutyl tin dichloride, butyl tin trichloride, tributyl tin cyanide, dibutyl tin dilaurate, dibutyl tin diacetate, dibutyl tin dioctoate, tributyl tin octoate, diphenyl tin dioctoate, dibutyl tin dibutoxy, dibutyl tin bis(acetylacetoate), dibutyl tin bis(isooctylmaleate), dioctoate tin oxide, dibutyl tin sulfide, stannous oleate, stannous tartrate, plumbous benzoate, stannous octoate, plumbous octanoate, plumbous oleate, lead naphthenate, antimony trichloride, antimony pentachloride, triphenyl stibium dichloride, triphenyl stibium, bismuth naphthenate, and diethyl bismuth acetate.

Preferably, the catalyst is a metal-containing catalyst. More preferably, the metal-containing catalyst represents at least one of tin tetrachloride, tetrabutyl tin, tributyl tin chloride, butyl tin dichloride, butyl tin trichloride, tributyl tin cyanide, dibutyl tin diacetate, dibutyl tin dioctanoate, tributyl tin octanoate, diphenyl tin dioctanoate, dibutoxy dibutyl tin, dibutyl tin bis(acetylacetoate), dibutyl tin bis (isooctylmaleate), dioctanoate tin oxide, dibutyl tin sulfide, stannous oleate, stannous tartrate, dibutyl tin dilaurate, stannous octanoate, or metal naphthenate. More preferably, the metal-containing catalyst may be metal naphthenate. More preferably, the naphthenate metal represents at least one of copper naphthenate, zinc naphthenate, lead naphthenate, lithium naphthenate, cobalt naphthenate, nickel naphthenate, cadmium naphthenate, mercury naphthenate, indium naphthenate, or bismuth naphthenate.

In some embodiments, the catalyst may not be added, and the reactant B may directly react with the tertiary amine or pyridine substituted by a terminal amino, a terminal hydroxyl or a terminal thiol.

React the mixture with a reactant A, and generate the antibacterial compound;

wherein, the reactant A represents propane sultone, butane sultone, β-propiolactone, $X(CH_2)_vCO_2—Mt^+$, $X(CH_2)_vSO_3—Mt^+$, or cyclic phosphate ester, the X represents Br, Cl, or I, v is an integer greater than 0, $Mt^+$ represents $Li^+$, $Na^+$, $K^+$, $NH_4^+$, $Ag^+$, $\frac{1}{2}Mg^{2+}$, or $\frac{1}{2}Ca^{2+}$, and the cyclic phosphate ester represents:

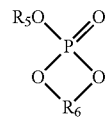

wherein, $R_5$ represents a monovalent unsubstituted or substituted alkyl, cycloalkyl, or aryl having from 1 to 6 carbon atoms; and $R_6$ represents a divalent unsubstituted or substituted alkyl having from 1 to 6 carbon atoms.

In the reactant A, since the carbon atom bound to the oxygen atom in propane sultone and butane sultone is liable to receive an attack from a nucleophile, while the mixture generated in the first step of the reaction include a tertiary amine nitrogen atom with good nucleophilicity, a ring-opening reaction can occur between the reactant A and the mixture generated in the first step of the reaction, forming a C—N bond. Therefore, a linking group is added to the tertiary nitrogen atom in the tertiary amine and form a quaternary ammonium group, which forms a zwitterionic compound together with a sulphonic acid group.

When the reactant A is cyclic phosphate ester (e.g., 2-ethoxy-2-oxy-1,3,2-dioxaphospholane, i.e., EOP), the carbon atom bound to the oxygen atom in the ring may receive an attack from the tertiary nitrogen atom, and a ring-opening reaction may occur, so that the tertiary nitrogen atom become a quaternary ammonium group which forms a zwitterionic compound together with a phosphoric acid group. Additionally, rings in the propiolactone and butyrolactone may also be liable to be opened due to a large ring strain and a small atom number, so that a ring-opening reaction may also occur in the presence of the tertiary nitrogen atom with strong nucleophilicity, forming a quaternary ammonium group and generating a carboxyl, and a zwitterionic compound may be formed.

Similarly, in $X(CH_2)_vCO_2$—Mt and $X(CH_2)_vSO_3$—Mt$^+$, since X (halogen such as Cl, Br, I) atom has large electronegativity and the bond formed with the carbon atom is weak, the X is easier to leave, the carbon atom bound thereto is liable to be attacked by the nucleophile, so that a C—N bond may be formed under an attack of the tertiary nitrogen atom, forming a quaternary ammonium group, which forms a zwitterionic compound together with a carboxyl or sulphonic acid group. Similarly, a similar nucleophilic substitution reaction may occur in metal carboxylate substituted by other leaving groups including but not limited to p-tosyl (-OTs), mesyl (-OMs) or trifluoromesyl (-OTf).

A solvent for preparing the antibacterial compound may include but not limited to organic solvents such as ethers, ketones, aromatic compounds, nitriles, esters or amides. A solvent itself may also be a mixture of several solvents, e.g., a mixture of two or more solvents. The solvent may be chosen according to a reactant solubility, a temperature of reaction, and a chemical reactivity of the solvent. Generally, a solvent easy to react with —N=C=O, such as water, alcohols, amines or carboxylic acid, is not suitable as a solvent for this reaction. Therefore, the solvent used in this embodiment needs to be previously dewatered, alcohol removed, and the like.

More preferably, the ether solvent may be THF, 1,4-dioxan ring, glycol dimethyl ether or tetrahydropyrane, etc.; the ketone solvent may be acetone, butanone, cyclohexanone, hypnone or phorone, etc.; the aromatic compounds may be toluene, pyridine or imidazole, etc.; esters may be ethyl acetate, n-propyl acetate, n-butyl acetate, methyl formate or ethyl formate, etc.; nitriles may be acetonitrile, propionitrile or benzonitrile, etc.; amides may be N-methylpyrrolidone, N,N-dimethylformamide or N,N-dimethylacetamide etc. The above is merely an example of a common solvent that can be used in this reaction and is not intended to limit the scope of the solvent.

In fact, any aprotic solvent which can dissolve the reaction raw materials may be used as a reaction solvent, e.g., ethylene carbonate and trimethylene carbonate.

The stirring method used in preparing the antibacterial compound may be a mechanical or magnetic stirring method in which the reactants can be sufficiently contacted.

The addition of the reactant solution may be manually dropping or dropping using a mechanical drip machine, and the dropping speed may be constant or may be continuously changed as the reaction progresses.

As for separation of the final product, different separation methods may be used according to different forms of the final product, as a non-precipitate, the final product can be purified by extraction or distillation; as a precipitate, the final product can be purified by centrifugation, filtration, and the like.

According to another aspect of the present disclosure, a method for preparing the antibacterial compound may include the following steps:

1) React pyridine represented by the general formula (V) with a reactant B represented by the general formula (IV), and generate a mixture;

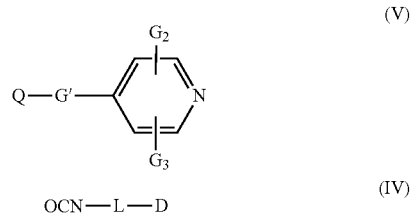

$$OCN-L-D \qquad (IV)$$

Wherein, the Q represents —OH, —NH$_2$, or —SH; G' represents a divalent unsubstituted or substituted alkyl, cycloalkyl, or aryl having from 1 to 18 carbon atoms; G$_2$ and G$_3$ independently for each occurrence represent —H, —F, —Cl, —Br, —I, —OCH$_3$, —OCH$_2$CH$_3$, —OPr, —CN, —SCN, —NO, —NO$_2$, a monovalent unsubstituted or substituted alkyl, cycloalkyl, or aryl having from 1 to 7 carbon atoms; D represents —COOH or —NCO; and L represents a divalent unsubstituted or substituted alkyl, cycloalkyl, or aryl having from 1 to 18 carbon atoms.

In this reaction, a typical nucleophilic addition reaction may occur between the functional group Q (—OH, —SH, —NH$_2$) in the pyridine represented by the general formula (V), and the isocyanate functional group (—NCO) in the reactant B represented by the general formula (IV), and generate a carbamate, thiocarbamate or urea structure. In the reaction, an atom (O, S, N) with large electronegativity in the functional group Q includes lone pair electrons, and the carbon atom in the isocyanate functional group is liable to have an additive reaction with a nucleophile, due to lack of electrons, to form a carbamate, thiocarbamate or urea structure.

In the presence of an alkaline reagent (such as tertiary amine, phosphines), the hydrogen atom in the Q functional group may also be removed in the form of a hydrogen ion, the nucleophilicity of O, S, and N atoms in the Q functional group may be further improved, so that the alkaline reagent may be used as a catalyst. While, in the presence of a Lewis acid such as a metal ion and an organometallic compound, the oxygen atom in the isocyanate may form a coordination bond with the Lewis acid, a part of electrons are transferred onto the metal atom from the oxygen atom, so that the electropositivity of the carbon atom in the isocyanate may be further enhanced, which facilitates receiving an attack from the nucleophile, and thus the Lewis acid may be used as a catalyst.

In a preparation using a catalyst, preferably, the catalyst may be one, two, or a combination of an organic amine compound, a phosphorus compound, and a metal-containing catalyst.

The organic amine compound may be classified to several categories: aliphatic amines, such as N,N-dimethyl cyclohexane, bis(2-dimethylamino ethyl)ether, N,N,N',N'-tetramethyl alkylene diamine, triethylamine, or N,N-dimethyl benzylamine; alicyclic amines, such as triethylene diamine (DABCO), N-ethyl morpholine, N-methyl morpholine, N,N'-diethyl piperazine, or dimethylamino cyclohexane; and aromatic amines, such as N,N-dimethyl aniline, pyridin, or 4-dimethylamino pyridine (N,N-dimethyl pyridine). A common property of the amine compounds include that they are all alkaline and may accelerate the reaction. Meanwhile, the amine compounds all include a tertiary nitrogen atom or a pyridine nitrogen atom, and thus do not include an active N—H or O—H bond and cannot react with the isocyanate.

Similar to the amine compounds, the phosphorus compounds may also function as an alkaline and accelerate the reaction. The phosphorus compounds may include but not limited to various tertiary phosphines in which three organic groups substituting three hydrogen atoms may be completely the same or completely different. Tertiary phosphines substituted by three same organic groups may include but not limited to triphenyl phosphine, trimethyl phosphine, triethyl phosphine, tri-n-propyl phosphine, triisopropyl phosphine, tri-n-butyl phosphine, or tri-t-butyl phosphine. Tertiary phosphines substituted by three different organic groups may include but not limited to dimethyl phenyl phosphine, methyl diphenyl phosphine, diethyl phenyl phosphine, or ethyl diphenyl phosphine.

In the metal-containing catalyst, since the metal ion may generally bind to the oxygen atom in the isocyanate to form a complex, electrons in the oxygen atom may transfer onto the metal atom, which enhances the electropositivity of the carbon atom bound thereto, facilitating the carbon atom receiving an attack from the nucleophile. The metal-containing catalyst may include but not limited to an inorganic metal salt, carboxylate, phenolate, metal alkylates, wherein carboxylate may be classified to linear or branched carboxylate and cyclic naphthenate. The metal elements contained are mainly alkali metals (lithium, sodium, potassium, rubidium, cesium, etc.); alkali earth metals (magnesium, calcium, strontium, barium); transition metals (uranium, cerium, titanium, zirconium, vanadium, chromium, molybdenum, manganese, ferrum, cobalt, nickel, copper, zinc, cadmium, mercury, etc.), aluminum, gallium, indium, thallium, tin, plumbum, stibium, bismuth, etc., but not limited thereto.

Common metal-containing catalysts may include but not limited to lithium acetate, lithium octanoate, lithium naphthenate, sodium trichlorphenate, sodium stearate, potassium acetate, potassium octanoate, calcium acetate, calcium octanoate, strontium naphthenate, barium acetate, uranyl nitrate, cerium nitrate, titanium tetrachloride, dibutyl titanium dichloride, titanium tetrabutyl, butoxy titanium trichloride, zirconium naphthenate, zirconium octanoate, vanadium trichloride, chromium naphthenate, molybdenum hexacarbonyl, manganese octanoate, ferric trichloride, ferrum octanoate, ferrum triacetylacetonate, ferrocene, cobalt octanoate, cobalt naphthenate, cobalt linoleate, cobalt benzoate, nickelocene, nickel octanoate, nickel naphthenate, copper acetate, copper octanoate, copper naphthenate, zinc octanoate, zinc naphthenate, cadmium nitrate, cadmium naphthenate, mercury diphenyl, mercury naphthenate, aluminum triphenyl, aluminium stearate, gallium acetate, indium naphthenate, thallium octanoate, tin tetrachloride, tin tetrachloride, etrabutyl tin, tributyl tin chloride, dibutyl tin dichloride, butyl tin trichloride, tributyl tin cyanide, dibutyl tin dilaurate, dibutyl tin diacetate, dibutyl tin dioctoate, tributyl tin octoate, diphenyl tin dioctoate, dibutyl tin dibutoxy, dibutyl tin bis(acetylacetoate), dibutyl tin bis(isooctylmaleate), dioctoate tin oxide, dibutyl tin sulfide, stannous oleate, stannous tartrate, plumbous benzoate, stannous octoate, plumbous octanoate, plumbous oleate, lead naphthenate, antimony trichloride, antimony pentachloride, triphenyl stibium dichloride, triphenyl stibium, bismuth naphthenate, and diethyl bismuth acetate.

Preferably, the catalyst is a metal-containing catalyst. More preferably, the metal-containing catalyst represents at least one of tin tetrachloride, tetrabutyl tin, tributyl tin chloride, butyl tin dichloride, butyl tin trichloride, tributyl tin cyanide, dibutyl tin diacetate, dibutyl tin dioctanoate, tributyl tin octanoate, diphenyl tin dioctanoate, dibutoxy dibutyl tin, dibutyl tin bis(acetylacetoate), dibutyl tin bis (isooctylmaleate), dioctanoate tin oxide, dibutyl tin sulfide, stannous oleate, stannous tartrate, dibutyl tin dilaurate, stannous octanoate, or metal naphthenate. More preferably, the metal-containing catalyst may be metal naphthenate. More preferably, the naphthenate metal represents at least one of copper naphthenate, zinc naphthenate, lead naphthenate, lithium naphthenate, cobalt naphthenate, nickel naphthenate, cadmium naphthenate, mercury naphthenate, indium naphthenate, or bismuth naphthenate.

In some embodiments, the catalyst may not be added, and the reactant B may directly react with the tertiary amine or pyridine substituted by a terminal amino, a terminal hydroxyl or a terminal thiol.

In the first step of the reaction, the nitrogen atom in the pyridine compound does not participate in the reaction. The function of the pyridine compound lies in that, firstly it provide a nucleophilic functional group Q to react with the reactant B having the isocyanate; secondly, the pyridine nitrogen atom in the pyridine compound is the parent of the quaternary ammonium salt in the final antibacterial compound, and the pyridine nitrogen atom may become a quaternary nitrogen atom, i.e. a pyridine quaternary ammonium salt structure, due to a new formation of a C—N bond in the subsequent synthesis. The number of carbon atoms in the pyridine compound has no effect on the reaction, as long as the pyridine compound include a group that can react with the isocyanate, such as a hydroxyl, a thiol or an amino, i.e. the first step of the reaction may take place.

A common property of the pyridine for preparing the antibacterial compound lies in that they all include one or more groups having an active hydrogen atom, such as a hydroxyl, an amino, and thiol, by which the pyridine compound can react with the isocyanate to couple with the same.

Exemplary pyridine may include but not limited to 4-hydroxymethylpiperidine, 4-aminopyridine, 4-mercaptopyridine or 2,6-dimethyl-4-aminopyridine. The hydrogen atom in the pyridine ring may be substituted by a substituent such as halogen (—F, —Cl, —Br, —I) or pseudohalogen (—CN, —SCN, —OCN, etc.), an alkoxyl (—$OCH_3$, —$OCH_2CH_3$, —OPr), —NO or $NO_2$, or an alkyl having from 1 to 7 carbon atoms or an aryl, the number of substitutes being at most 7.

2) React the mixture with a reactant A, and generate the antibacterial compound;

The reactant A represents propane sultone, butane sultone, β-propiolactone, $X(CH_2)_vCO_2$—$Mt^+$, $X(CH_2)_vSO_3$—$Mt^+$, or cyclic phosphate ester, the X represents Br, Cl, or I, v is an integer greater than 0, $Mt^+$ represents $Li^+$, $Na^+$, $K^+$, $NH_4^+$, $Ag^+$, $\frac{1}{2}Mg^{2+}$, or $\frac{1}{2}Ca^{2+}$, and the cyclic phosphate ester represents:

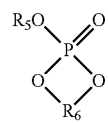

wherein, $R_5$ represents a monovalent unsubstituted or substituted alkyl, cycloalkyl, or aryl having from 1 to 6 carbon atoms; and $R_6$ represents a divalent unsubstituted or substituted alkyl having from 1 to 6 carbon atoms.

In the reactant A, since the carbon atom bound to the oxygen atom in sultone is liable to receive an attack a the nucleophile, while the mixture generated in the first step of the reaction include a tertiary nitrogen atom with good nucleophilicity, a ring-opening reaction can occur between the reactant A and the mixture generated in the first step of the reaction, forming a C—N bond. Therefore, a linking group is added to the tertiary nitrogen atom in the tertiary amine and form a quaternary ammonium group, which forms a zwitterionic compound together with a sulphonic acid group. Similar to sultone, the carbon atom bound to the oxygen atom in the cyclic phosphate ester may receive an attack from the tertiary nitrogen atom and a ring-opening reaction may occur, so that the tertiary nitrogen atom become a quaternary ammonium group which forms a zwitterionic compound together with a phosphoric acid group. Additionally, rings in the propiolactone and butyrolactone may also be liable to be opened due to a large ring strain and a small atom number, so that a ring-opening reaction may also occur in the presence of the tertiary nitrogen atom with strong nucleophilicity, forming a quaternary ammonium group and generating a carboxyl, and thus a zwitterionic compound is formed. In $X(CH_2)_xCO_2$—$Mt$ and $X(CH_2)_xSO_3$—$Mt^+$, since X (halogen such as Cl, Br, I) atom has large electronegativity and the bond formed with the carbon atom is weak, the X is easier to leave, the carbon atom bound thereto is liable to be attacked by the nucleophile, so that a C—N bond may be formed under an attack of the tertiary nitrogen atom, forming a quaternary ammonium group, which forms a zwitterionic compound together with a carboxyl or sulphonic acid group. Similarly, a similar nucleophilic substitution reaction may occur in metal carboxylate substituted by other leaving groups including but not limited to p-tosyl (-OTs), mesyl (-OMs) or trifluoromesyl (-OTf).

A solvent for preparing the antibacterial compound may include but not limited to organic solvents such as ethers, ketones, aromatic compounds, nitriles, esters or amides. A solvent itself may also be a mixture of several solvents, e.g., a mixture of two or more solvents. The solvent may be chosen according to a reactant solubility, a temperature of reaction, and a chemical reactivity of the solvent. Generally, a solvent easy to react with —N═C═O, such as water, alcohols, amines or carboxylic acid, is not suitable as a solvent for this reaction. Therefore, the solvent used in this embodiment needs to be previously dewatered, alcohol removed, and the like.

More preferably, the ether solvent may be THF, 1,4-dioxan ring, glycol dimethyl ether or tetrahydropyrane, etc.; the ketone solvent may be acetone, butanone, cyclohexanone, hypnone or phorone, etc.; the aromatic compounds may be toluene, pyridine or imidazole, etc.; esters may be ethyl acetate, n-propyl acetate, n-butyl acetate, methyl formate or ethyl formate, etc.; nitriles may be acetonitrile, propionitrile or benzonitrile, etc.; amides may be N-methylpyrrolidone, N,N-dimethylformamide or N,N-dimethylacetamide etc. The above is merely an example of a common solvent that can be used in this reaction and is not intended to limit the scope of the solvent.

The above is merely an example of a common solvent that can be used in this reaction and is not intended to limit the scope of the solvent. In fact, any aprotic solvent which can dissolve the reaction raw materials may be used as a reaction solvent, e.g., ethylene carbonate and trimethylene carbonate.

The stirring method used in preparing the antibacterial compound may be a mechanical or magnetic stirring method in which the reactants can be sufficiently contacted.

The addition of the reactant solution may be manually dropping or dropping using a mechanical drip machine, and the dropping speed may be constant or may be continuously changed as the reaction progresses.

As for separation of the final product, different separation methods may be used according to different forms of the final product; as a non-precipitate, the final product can be purified by extraction or distillation; as a precipitate, the final product can be purified by centrifugation, filtration, and the like.

Raw materials and other chemical agents used in the following examples are commercially available. If necessary, the raw materials and other chemical agents may be purified by methods known in the art, such as removal of water, oxidized components, primary and secondary amines in tertiary amines, etc., which can be carried out by means of distillation, splitting, extraction, or addition of reagents.

Example 1

44.6 g (0.2 mol) isophorone diisocyanate (IPDI) represented by:

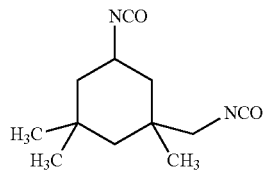

was weighted and added to a round flask with mechanical stirring. After adding a catalyst of 0.2 ml dibutyl tin dilaurate (DBTDL), 17.8 g (0.2 mol) dimethyl ethanolamine ($HOCH_2CH_2N(CH_3)_2$) was slowly dropwise added thereto, using a dropping funnel under stirring at the temperature of 30° C. After the dropwise addition, the reaction was continued for 1 h, and the stirring was continued for 12 h at this temperature. Then, 24.4 g (0.2 mol) propane sultone (hereinafter referred to as 1,3-PS, with a structure as follows),

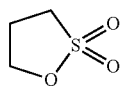

dissolved in 400 mL anhydrous THF was dropwise added. After the dropwise addition, the reaction was continued for 1 h and generate a precipitate, which was centrifuged and purified for several times to afford the antibacterial compound having a terminal isocyanate according to the example.

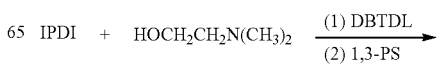

-continued

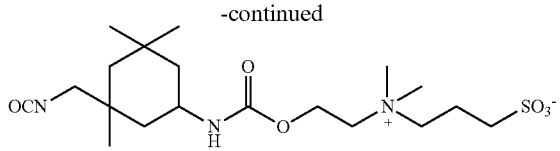

In this example, isophorone diisocyanate was used as a reactant having the isocyanate. It should be understood that a similar antibacterial compound having a terminal isocyanate can be obtained via the above reaction through any compound having at least two isocyanates. Since a polyisocyanate compound may include a plurality of isocyanates, only one isocyanate of the plurality of isocyanates in a molecule is reacted, and other isocyanates are reserved in the final antibacterial compound when a nucleophile is not excessive. The number of carbon atoms or the molecular weight of the polyisocyanate compound has no effect on the reaction, as long as a nucleophilic addition reaction can occur between the polyisocyanate compound and the nucleophile. In this example, the isocyanate structure may also be a terminal isocyanate organic compound having at least one carboxyl, a backbone structure of the organic compound may include an unsubstituted or substituted aliphatic, alicyclic, heterochain, heterocyclic, aromatic structure, wherein the substituent may include but not limited to —Cl, —Br, —I, —OCH$_3$, —OCH$_2$CH$_3$, —OPr, —CN, —SCN, —NO, —NO$_2$, etc.

In the reaction, the function of propane sultone is to open a five-membered ring by receiving a nucleophilic attack from the tertiary amine N atom and thus to form a sulphonic acid group, meanwhile forming a quaternary ammonium group. Since the carbon atom bound to the oxygen atom in sultone is liable to receive an attack from the nucleophile, while the mixture generated in the first step of the reaction includes a tertiary nitrogen atom with good nucleophilicity, a ring-opening reaction can occur between the reactant A and the mixture generated in the first step of the reaction, forming a C—N bond. Therefore, a linking group is added to the tertiary nitrogen atom in the tertiary amine to form a quaternary ammonium group, which forms a zwitterionic compound together with a sulphonic acid group. Similarly, other sultones such as butane sultone and ethane sultone may also be used in the second step of the reaction since a similar reaction may take place.

Although dibutyl tin dilaurate was used as a catalyst in this example, a catalyst is not always necessary and an organic amine compound having higher activity can react directly with a compound having a plurality of isocyanates in the absence of the catalyst. In a preparation using a catalyst, preferably, the catalyst may be one, two, or a combination of an organic amine compound, a phosphorus compound, and a metal-containing catalyst. For example, triethylamine, triphenyl phosphine, dibutyl tin dioctanoate.

In some embodiments, the catalyst may not be added, and the reactant B may directly react with the tertiary amine or pyridine substituted by a terminal amino, a terminal hydroxyl or a terminal thiol.

In addition to N,N-dimethyl ethanolamine, amines for preparation in this example may also be N,N-diethyl ethanolamine, N,N-dimethyl ethylenediamine, N,N-di-n-propyl ethanolamine, N,N-diisopropyl ethanolamine, N,N-di-n-butyl ethanolamine, N,N-di-n-pentyl ethanolamine, N,N-dicyclohexyl ethanolamine, or 3,3'-iminobis(N,N-dimethyl propylamine).

Moreover, although amines were used in this example, tertiary amines or pyridine organic compounds having a terminal alcohol group or terminal thiol may be used, such as 4-hydroxymethylpiperidine and 2,6-dimethyl-4-aminopyridine.

Example 2

50.1 g (0.2 mol) diphenylmethane diisocyanate (MDI) was weighted and added to a round flask with mechanical stirring. After adding a catalyst of 0.2 ml dibutyl tin dilaurate, 23.5 g (0.2 mol) N,N-diethyl ethanolamine (HOCH$_2$CH$_2$N(CH$_2$CH$_3$)$_2$) was slowly dropwise added thereto, using a dropping funnel under stirring at the temperature of 30° C. After the dropwise addition, the reaction was continued for 1 h, and the stirring was continued for 12 h at this temperature. Then, 24.4 g (0.2 mol) propane sultone dissolved in 400 mL anhydrous THF was dropwise added. After the dropwise addition, the reaction was continued for 1 h and generate an oil, which was extracted by a polar aprotic solvent DMSO, solvent removed, and purified to afford the antibacterial compound having a terminal isocyanate according to this example.

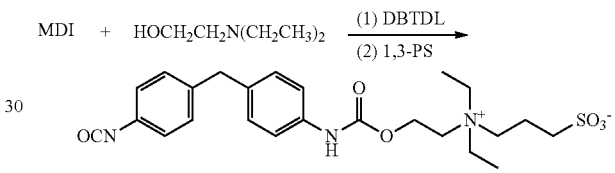

Example 3

33.6 g (0.2 mol) hexamethylene diisocyanate (HDI) was weighted and added to a round flask with mechanical stirring. After adding a catalyst of 0.2 ml stannous octanoate (Sn(CH$_3$(CH$_2$)$_3$CH(C$_2$H$_5$)CO$_2$)$_2$), 17.8 g (0.2 mol) N,N-dimethyl ethanolamine (HOCH$_2$CH$_2$N(CH$_3$)$_2$) was slowly dropwise added thereto, using a dropping funnel under stirring at the temperature of 30° C. After the dropwise addition, the reaction was continued for 1 h, and the stirring was continued for 12 h at this temperature. Then, 23.6 g (0.2 mol) sodium chloroacetate (ClCH$_2$CO$_2$Na) dissolved in 400 mL anhydrous THF was dropwise added. The reaction was continued for 24 h under the temperature of 20° C. and generate a crude product, which was centrifuged and purified for several times to afford the antibacterial compound having a terminal isocyanate according to this example.

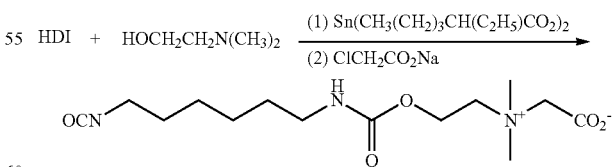

In the reaction, the function of sodium chloroacetate is to remove the chlorine atom by receiving a nucleophilic attack from the tertiary amine N atom and thus to form a quaternary ammonium group. Similarly, sodium carboxylate substituted by other halogen (Br, I, etc.) or other easily leaving groups (OTs, OMs, OTf, etc.), such as sodium bromoacetate, sodium iodoacetate, sodium 2-chloropropionate, sodium 3-chloropropionate, sodium 2-bromopropionate, sodium 3-bromopropionate, sodium 2-iodopropionate, sodium 3-iodopropionate, or halogenated carboxylate with a longer carbon chain, may also be used in the second step of the reaction, since the halogen is liable to be removed by the nucleophilic attack from the N atom and thus a similar reaction may take place.

The addition of the sodium chloroacetate solution may be manually dropping or dropping using a mechanical drip machine, and the dropping speed may be constant or may be continuously changed as the reaction progresses.

Example 4

34.8 g (0.2 mol) toluene diisocynate (a mixture including 2,4-toluene diisocynate and 2,6-toluene diisocynate) was weighted and added to a round flask with mechanical stirring. After adding a catalyst of 0.2 ml dibutyl tin dilaurate (DBTDL), 17.8 g (0.2 mol) dimethyl ethanolamine (HOCH$_2$CH$_2$N(CH$_3$)$_2$) was slowly dropwise added thereto, using a dropping funnel under stirring at the temperature of 30° C. After the dropwise addition, the reaction was continued for 1 h, and the stirring was continued for 12 h at this temperature. Then, to the filtrate, 14.4 g (0.2 mol) β-propiolactone represented by:

dissolved in 400 mL anhydrous THF was dropwise added. The reaction was continued for 6 h under the temperature of 40° C. to generate a product, which was filtered under normal pressure and purified to afford the antibacterial compound having a terminal isocyanate according to this example.

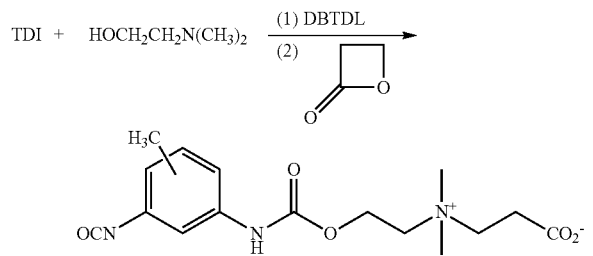

In the reaction, the function of β-propiolactone is to open a ring by receiving a nucleophilic attack from the tertiary amine N atom and thus to form a carboxyl, meanwhile forming a quaternary ammonium group. Similarly, other lactones, such as β-butyrolactone, γ-butyrolactone, β-valerolactone, γ-valerolactone may also be used in the second step of the reaction, since a similar reaction may take place to generate a corresponding zwitterionic compound.

The addition of the β-propiolactone solution may be manually dropping or dropping using a mechanical drip machine, and the dropping speed may be constant or may be continuously changed as the reaction progresses.

Example 5

52.5 g (0.2 mol) dicyclohexyl methane diisocyanate (HMDI) was weighted and added to a round flask with mechanical stirring. After adding a catalyst of 0.2 ml dibutyl tin dilaurate, 17.8 g (0.2 mol) N,N-dimethyl ethylenediamine (H$_2$NCH$_2$CH$_2$N(CH$_3$)$_2$) was slowly dropwise added thereto, using a dropping funnel under stirring at the temperature of 30° C. After the dropwise addition, the reaction was continued for 1 h, and the stirring was continued for 12 h at this temperature. Then, 24.4 g (0.2 mol) propane sultone dissolved in 400 mL anhydrous acetone was dropwise added. After the dropwise addition, the reaction was continued for 1 h and generate a precipitate, which was centrifuged and purified for several times to afford the antibacterial compound having a terminal isocyanate according to this example.

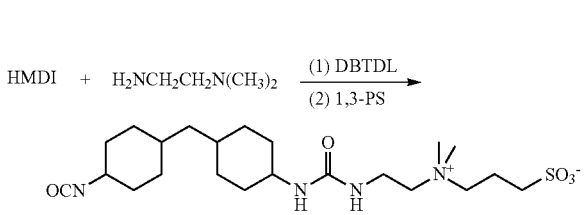

Example 6

44.6 g (0.2 mol) isophorone diisocyanate (IPDI) was weighted and added to a round flask with mechanical stirring. After adding a catalyst of 0.2 ml dibutyl tin dilaurate, 17.8 g (0.2 mol) N,N-dimethyl ethylenediamine (H$_2$NCH$_2$CH$_2$N(CH$_3$)$_2$) was slowly dropwise added thereto, using a dropping funnel under stirring at the temperature of 30° C. After the dropwise addition, the reaction was continued for 1 h, and the stirring was continued for 12 h at this temperature. Then, to the filtrate, 14.4 g (0.2 mol) β-propiolactone dissolved in 400 mL anhydrous butanone was dropwise added. The reaction was continued for 6 h under the temperature of 40° C. and generate a crude product, which was centrifuged and purified for several times to afford the antibacterial compound having a terminal isocyanate.

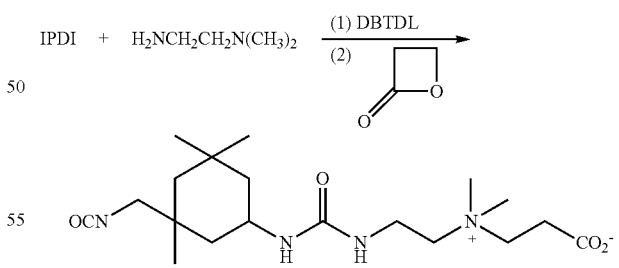

Example 7

44.6 g (0.2 mol) isophorone diisocyanate (IPDI) was weighted and added to a round flask with mechanical stirring. After adding a catalyst of 0.2 ml dibutyl tin dilaurate, 37.4 g (0.2 mol) 3,3'-iminobis(N,N-dimethyl propylamine) represented by:

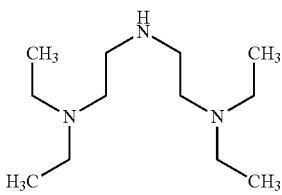

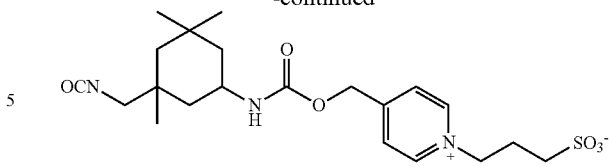

was slowly dropwise added thereto, using a dropping funnel under stirring at the temperature of 30° C. After the dropwise addition, the reaction was continued for 1 h, and the stirring was continued for 12 h at this temperature. Then, 48.8 g (0.4 mol) propane sultone dissolved in 400 mL anhydrous ethyl acetate was dropwise added. After the dropwise addition, the reaction was continued for 1 h and generate a crude product, which was centrifuged and purified for several times to afford the antibacterial compound having a terminal isocyanate.

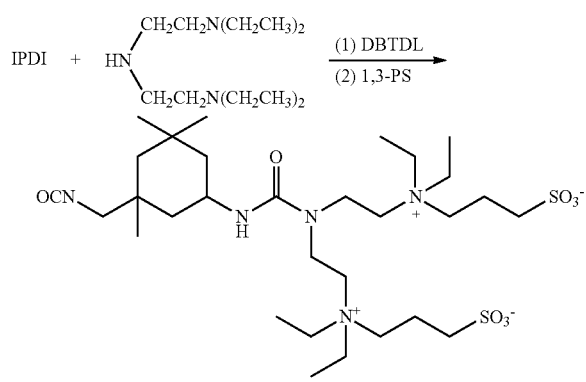

In addition to 3,3'-iminobis(N,N-dimethyl propylamine), amines for preparation in this example may also be other tertiary amine or pyridine having an active hydrogen atom, such as but not limited to N,N-dimethyl ethanolamine, N,N-dimethyl ethylenediamine, N,N-diethyl ethanolamine, N,N-diisopropyl ethanolamine, N,N-di-n-butyl ethanolamine, N,N-di-n-pentyl ethanolamine, N,N-dicyclohexyl ethanolamine, 4-hydroxymethylpiperidine or 2,6-dimethyl-4-aminopyridine.

Example 8

44.6 g (0.2 mol) isophorone diisocyanate (IPDI) was weighted and added to a round flask with mechanical stirring. After adding a catalyst of 0.2 ml dibutyl tin dilaurate, 21.8 g (0.16 mol) 4-hydroxymethylpiperidine was slowly dropwise added thereto, using a dropping funnel under stirring at the temperature of 30° C. After the dropwise addition, the reaction was continued for 1 h, and the stirring was continued for 12 h at this temperature. Then, 24.4 g (0.2 mol) propane sultone dissolved in 400 mL anhydrous THF was dropwise added. After the dropwise addition, the reaction was continued for 1 h and generate a crude product, which was centrifuged and purified for several times to afford the antibacterial compound having a terminal isocyanate.

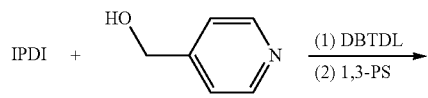

The nitrogen-containing compound for preparation in this example includes a functional group having an active hydrogen atom such as a hydroxyl, an amino or a thiol, and may be pyridine compounds or tertiary amines, which may be substituted or unsubstituted aliphatic, alicyclic or aromatic. In addition to 4-hydroxymethylpiperidine, the nitrogen-containing compound may also be 2,6-dimethyl-4-aminopyridine, N,N-dimethyl ethanolamine, N,N-dimethyl ethylenediamine, N,N-diethyl ethanolamine, N,N-diisopropyl ethanolamine, N,N-di-n-butyl ethanolamine, N,N-di-n-pentyl ethanolamine, N,N-dicyclohexyl ethanolamine, 3,3'-iminobis(N,N-dimethyl propylamine), 4-methylpyridine, or 2,6-dimethyl-4-aminopyridine, etc. The above is merely examples of an optional amine/pyridine compound and is not intended to limit the scope of the nitrogen-containing compound in this reaction, and any pyridine or tertiary amine compound having an active hydrogen atom may be used as a reactant, for example, 4-hydroxypyridine.

Example 9

44.6 g (0.2 mol) isophorone diisocyanate (IPDI) was weighted and added to a round flask with mechanical stirring. After adding a catalyst of 0.2 ml stannous octanoate, 24.4 g (0.2 mol) 2,6-dimethyl-4-aminopyridine was slowly dropwise added thereto, using a dropping funnel under stirring at the temperature of 30° C. After the dropwise addition, the reaction was continued for 1 h, and the stirring was continued for 12 h at this temperature. Then, 24.4 g (0.2 mol) propane sultone dissolved in 400 mL anhydrous THF was dropwise added. After the dropwise addition, the reaction was continued for 1 h and generate a crude product, which was centrifuged and purified for several times to afford the antibacterial compound having a terminal isocyanate.

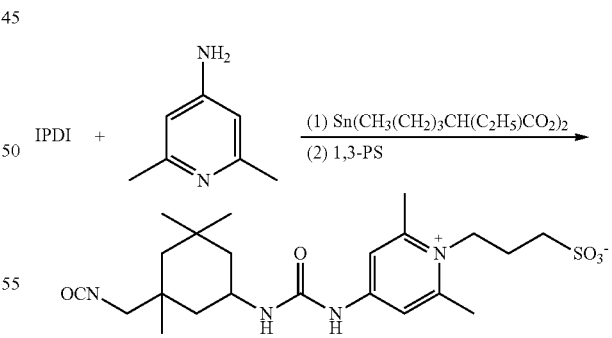

Although stannous octanoate was used as a catalyst in this example, a catalyst is not always necessary and an organic amine compound having higher activity can react directly with a compound having a plurality of isocyanates in the absence of the catalyst. In a preparation using a catalyst, materials used as a catalyst may be described according to Example 1.

The nitrogen-containing compound used in this example for preparation, includes a group having an active hydrogen atom such as an amino, a hydroxyl, or a thiol, in addition to pyridine nitrogen atoms or tertiary amine nitrogen atoms in the structure thereof. As an example, in addition to 2,6-dimethyl-4-aminopyridine, the nitrogen-containing compound may also be N,N-dimethyl ethanolamine, N,N-dimethyl ethylenediamine, N,N-diethyl ethanolamine, N,N-diisopropyl ethanolamine, N,N-di-n-butyl ethanolamine, N,N-di-n-pentyl ethanolamine, N,N-dicyclohexyl ethanolamine, 3,3'-iminobis(N,N-dimethyl propylamine), 4-hydroxymethylpiperidine, 4-thiomethylpyridine, 2-dimethylamino ethanethiol, 2-diethylamino ethanethiol, 2-dimethylamino propanethiol, 2-diethylamino propanethiol, 2,6-diethyl-4-aminopyridine, or 4-aminopyridine whose 2-position or 6-position is substituted by other alkyl, halogen (—F, —Cl, —Br, —I), $NO_2$ or an alkoxyl, etc.

Example 10

44.6 g (0.2 mol) isophorone diisocyanate (IPDI) was weighted and added to a round flask with mechanical stirring. After adding a catalyst of 0.2 ml dibutyl tin dilaurate, 17.8 g (0.2 mol) dimethyl ethanolamine ($HOCH_2CH_2N(CH_3)_2$) was slowly dropwise added thereto, using a dropping funnel under stirring at the temperature of 30° C. After the dropwise addition, the reaction was continued for 1 h, and the stirring was continued for 12 h at this temperature. Then, 42.2 g (0.2 mol) sodium 2-bromoethanesulfonate dissolved in 400 mL anhydrous THF was dropwise added. After the dropwise addition, the reaction was continued for 1 h and generate a crude product, which was centrifuged and purified for several times to afford the antibacterial compound having a terminal isocyanate.

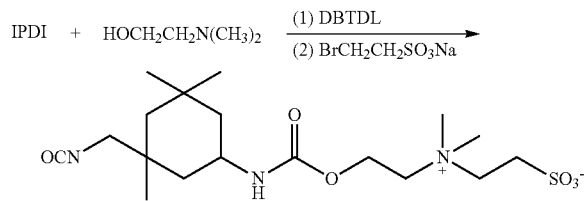

In the reaction, the function of sodium 2-bromoethanesulfonate is to remove the bromine atom by receiving a nucleophilic attack from the N atom and thus to form a quaternary ammonium group, forming a final zwitterionic compound. Similarly, sodium sulfonate substituted by other halogen or other easily leaving groups, such as sodium 2-chloroethanesulfonate, sodium 2-iodoethanesulfonate, sodium 2-chloropropanesulfonate, sodium 2-bromopropanesulfonate, sodium 2-iodopropanesulfonate, or sodium 2-p-(phenylsulfonyl)propanesulfonate, may also be used in the second step of the reaction, since a similar reaction may take place.

The addition of the sodium 2-bromoethanesulfonate solution may be manually dropping or dropping using a mechanical drip machine, and the dropping speed may be constant or may be continuously changed as the reaction progresses.

Example 11

44.6 g (0.2 mol) isophorone diisocyanate (IPDI) was weighted and added to a round flask with mechanical stirring. After adding a catalyst of 0.2 ml dibutyl tin dilaurate, 17.8 g (0.2 mol) dimethyl ethanolamine ($HOCH_2CH_2N$ $(CH_3)_2$) was slowly dropwise added thereto, using a dropping funnel under stirring at the temperature of 30° C. After the dropwise addition, the reaction was continued for 1 h, and the stirring was continued for 12 h at this temperature. Then, 37.4 g (0.22 mol) sodium 4-bromobutyrate dissolved in 400 mL anhydrous THF was dropwise added. After the dropwise addition, the reaction was continued for 1 h and generate a crude product, which was centrifuged and purified for several times to afford the antibacterial compound having a terminal isocyanate.

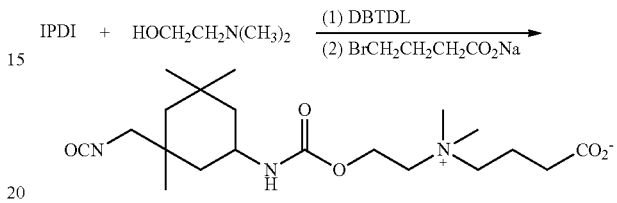

In the reaction, the function of sodium 4-bromobutyrate is to remove the bromine atom by receiving a nucleophilic attack from the N atom and thus to form a quaternary ammonium group. Similarly, metal carboxylate substituted by other halogen or other leaving groups. The halogen may include but not limited to chlorine, bromine, and iodine; other leaving groups may include but not limited to p-tosyl (-OTs), mesyl (-OMs), or trifluoromesyl (-OTf); the metal in metal carboxylate may include but not limited to lithium, sodium, potassium, ammonium, silver, magnesium, or calcium; carboxylic acid may include but not limited to acetic acid, propionic acid, butyric acid, valeric acid, or carboxylic acid having more carbon atoms; the position of halogen or other substituents may be α, β, γ positions approaching to the carbon atom in the carboxyl. Typical halogen substituted metal carboxylate may include but not limited to sodium chloroacetate, sodium bromoacetate, sodium iodoacetate, sodium 2-chloropropionate, sodium 3-chloropropionate, sodium 2-bromopropionate, sodium 3-bromopropionate, sodium 2-iodopropionate, sodium 3-iodopropionate, sodium 4-chlorobutyrate, or sodium 4-iodobutyrate. The above materials may also be used in the second step of the reaction, since they can similarly react with tertiary amines.

The addition of the sodium 4-bromobutyrate solution may be manually dropping or dropping using a mechanical drip machine, and the dropping speed may be constant or may be continuously changed as the reaction progresses.

As for separation of the final product, different separation methods may be used according to different forms of the final product; if the final product is an oil or sticky solid, the final product can be purified by extraction or distillation; if the final product is a precipitate, the final product can be purified by centrifugation or filtration or the like.

Example 12

9.3 g (0.2 mol) ethanol and 20.2 g (0.2 mol) triethylamine (TEA) were weighted and dissolved in 100 ml anhydrous THF. The mixture was added to a round flask with mechanical stirring, and was cooled at −20° C. for 20 min and maintained at −20° C. To the reaction vessel, 28.392 g (0.2 mol) 2-chloro-oxy-1,3,2-dioxaphospholane (COP) dissolved in 30 ml anhydrous THF was dropwise added. After the dropwise addition, the mixture was allowed to stand at −20° C. until a precipitate is generated. The precipitate was distilled under vacuum to give 2-ethoxy-2-oxy-1,3,2-dioxaphospholane (EOP).

44.6 g (0.2 mol) isophorone diisocyanate (IPDI) was weighted and added to a round flask with mechanical stirring. After adding a catalyst of 0.2 ml dibutyl tin dilaurate, 17.8 g (0.2 mol) dimethyl ethanolamine (HOCH$_2$CH$_2$N(CH$_3$)$_2$) was slowly dropwise added thereto, using a dropping funnel under stirring at the temperature of 30° C. After the dropwise addition, the reaction was continued for 1 h, and the stirring was continued for 12 h at this temperature. Then, 30.4 g (0.2 mol) EOP dissolved in 400 mL anhydrous THF was dropwise added at 75° C. After the dropwise addition, the reaction was continued for 24 h and generate a crude product, which was centrifuged and purified for several times to afford the antibacterial compound having a terminal isocyanate.

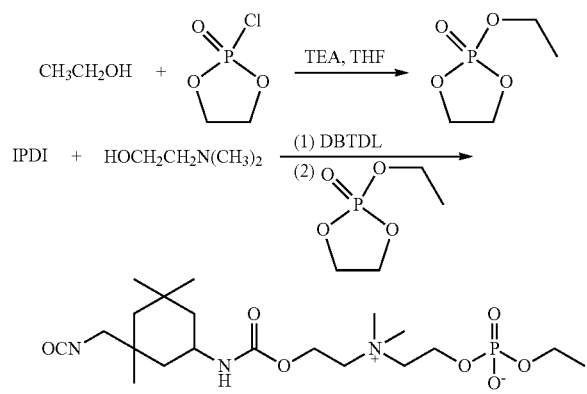

In the above reaction, ethanol attacked the P atom of COP, and HCl was lost, so that a substitution reaction has taken place to give the product EOP. Similarly, in addition to ethanol, those can react with COP in a substitution reaction may also be other fatty alcohols, alicyclic alcohols or aromatic alcohols, such as methanol, n-propanol, isopropanol, n-butanol, n-pentanol, n-heptanol, vinyl alcohol, propenol, cyclopropanol, cyclopentanol, cyclohexanol, or benzyl alcohol.

Although COP was used as a phosphorus-containing reagent in this example, the phosphorus-containing reagent may be other 2-halo-1,3,2-dioxaphosphorus heterocyclic compounds in which the number of atoms in the ring may be 4, 5, 6, 7, 8 or 9, preferably 5, 6, or 7, i.e., 2-halo-1,3,2-dioxaphospholane, 2-halo-1,3,2-dioxaphosphinan or 2-halo-1,3,2-dioxaphosphepine. In this reaction, the phosphorus atom in 2-halo-1,3,2-dioxaphosphorus heterocyclic compound may be bound to a halogen atom in addition to binding to the oxygen atom. As disclosed in U.S. Pat. No. 2,982,862, the halogen atom in this compound may include chlorine, bromine, or iodine which is easily substituted by the alkoxyl in alcohols due to a better leaving property. The hydrogen atom bound to the carbon atom in the ring may be substituted by one or more alkyls, such as methyl, ethyl, n-propyl, isopropyl, sec-butyl, isobutyl, or t-butyl.

In addition to COP, the compound may also include but not limited to 2-chloro-4,5-dimethyl-1,3,2-dioxaphospholane-2-oxide, 2-chloro-1,3,2-dioxaphosphinan-2-oxide, 2-chloro-5,5-dimethyl-4-phenyl-1,3,2-dioxaphosphinan-2-oxide, 2-chloro-4,6-dimethyl-1,3,2-dioxaphosphinan-2-oxide, 2-chloro-5,5-dimethyl-1,3,2-dioxaphosphinan-2-oxide, 2-chloro-1,3,2-dioxaphosphepine-2-oxide, 2-chloro-1,3,2-dioxaphosphocane-2-oxide, 2-bromo-1,3,2-dioxaphospholane-2-oxide, 2-bromo-1,3,2-dioxaphosphinan-2-oxide, or 2-bromo-5,5-dimethyl-1,3,2-dioxaphosphinan-2-oxide.

Although triethylamine was used as a reaction auxiliary in this example, other tertiary amines which do not contain active hydrogen may also be used, such as trimethylamine, tri-n-propylamine, tri-iso-propylamine, tri-n-butylamine, N-methyl dioctylamine, N,N-dimethyl cyclopentylamine or N,N-dimethyl cyclohexane. In this alcoholysis reaction, tertiary amine was used as alkali to assist in removing HCl.

Although THF was used as an organic solvent, the organic solvent may also be acetonitrile, DMF, DMSO, anhydrous butanone, anhydrous acetone, cyclohexanone, toluene, ethyl acetate, n-propyl acetate, n-butyl acetate, acetonitrile, 1,4-dioxan ring, N-methylpyrrolidone, pyridin, N,N-dimethylformamide, or a mixture of two or more solvents above.

In the second step of the reaction, the function of EOP is to make a ring-opening reaction occur by the C atom bound to the O atom in the ring receiving a nucleophilic attack from the N atom and thus to form a quaternary ammonium group.

The addition of the EOP solution may be manually dropping or dropping using a mechanical drip machine, and the dropping speed may be constant or may be continuously changed as the reaction progresses.

As for separation of the final product, different separation methods may be used according to different forms of the final product; if the final product is an oil, the final product can be purified by extraction or distillation; if the final product is a precipitate, the final product can be purified by centrifugation or filtration or the like.

Example 13

9.3 g (0.2 mol) ethanol and 20.2 g (0.2 mol) triethylamine (TEA) were weighted and dissolved in 100 ml anhydrous THF. The mixture was added to a round flask with mechanical stirring, and was cooled at −20° C. for 20 min and maintained at −20° C. To the reaction vessel, 28.392 g (0.2 mol) 2-chloro-5,5-dimethyl-1,3,2-dioxaphosphinan-2-oxide dissolved in 30 ml anhydrous THF was dropwise added. After the dropwise addition, the mixture was allowed to stand at −20° C. until a precipitate is generated. The precipitate was distilled under vacuum and purified to give 2-ethoxy-2-oxy-1,3,2-dioxaphosphinan.

50.1 g (0.2 mol) diphenylmethane diisocyanate (MDI) was added to a round flask with mechanical stirring. After adding a catalyst of 0.2 ml dibutyl tin dilaurate, 23.5 g (0.2 mol) N,N-diethyl ethanolamine (HOCH$_2$CH$_2$N(CH$_2$CH$_3$)$_2$) was slowly dropwise added thereto, using a dropping funnel under stirring at the temperature of 30° C. After the dropwise addition, the reaction was continued for 1 h, and the stirring was continued for 12 h at this temperature. Then, 30.4 g (0.2 mol) 2-ethoxy-2-oxy-1,3,2-dioxaphosphinan dissolved in 400 mL anhydrous THF was dropwise added at 70° C. After the dropwise addition, the reaction was continued for 24 h and generate a crude product, which was centrifuged and purified for several times to afford the antibacterial compound having a terminal isocyanate.

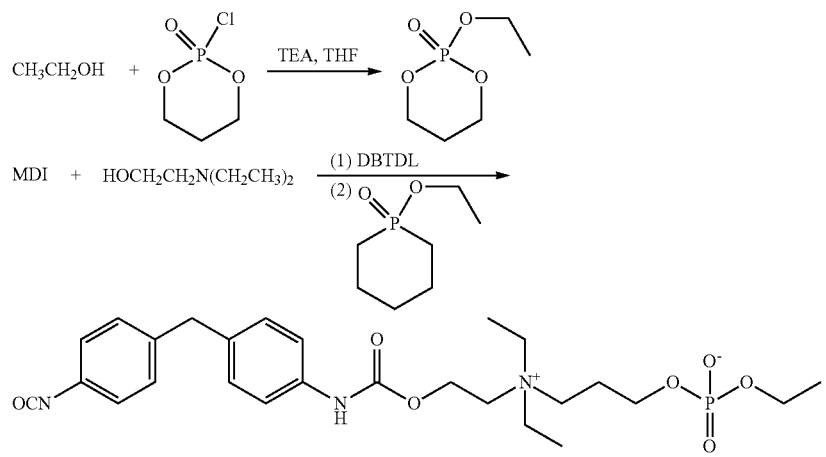

The antibacterial compound provided by this example of the present disclosure is a zwitterionic compound having a terminal isocyanate. The positive charge of a quaternary nitrogen atom may damage the cytomembrane of the microorganism, thereby denaturing the protein and damaging the cell structure. The microorganism may include but not limited to *E. coli*, *S. typhimurium*, *P. aeruginosa*, *S. aureas*, *C. albicans*, sulfate reducing bacteria, Gram-positive bacteria, Gram-negative bacteria, *S. epidermidis*, *E. faecalis*, *C. xerosis*, *B. anthracis*, etc. The antibacterial compound may be used as a sterilizing agent or a bacteriostatic agent to prevent infections, to kill microorganisms or to inhibit physiological functions of the microorganisms, and thus may effectively treat the infections caused by these microorganisms, or control pollution caused by the same.

The antibacterial compound provided by this example of the present disclosure may be chemically bound to the surface of the material through the terminal isocyanate. The antibacterial compound may be applied to textile, medicine, food, and agriculture fields, but not limited thereto. For example, the isocyanate may be bound to a hydroxyl or amino on the surface of a fiber, a cotton textile, or a nylon to produce a antibacterial textile with detergent resistance; may be bound to a hydroxyl or amino on the surface of a medical perfusion tube or packaging material to produce an antibacterial medical product; or may be bound to a hydroxyl or amino on the surface of a food package or food preservation material to produce an antibacterial packaging material.

The products according to Examples 1-13 of the present disclosure were tested for minimum inhibitory concentration of *E. coli* (American Type Culture Collection ATCC 25922) and *S. aureas* (ATCC 6538). The minimum inhibitory concentration (MIC) is the lowest concentration of antibacterial agents that can inhibit the visible growth of bacteria after 24 h culture in a specific environment. Methods for determining the minimum inhibitory concentration can be a constant broth dilution method, a trace broth dilution method, an agar dilution method or an E experiment. The antibacterial concentration test results of the antibacterial agents of Examples 1-13 of the present disclosure are shown in Table 1.

TABLE 1

Minimum inhibitory concentrations (MIC, unit: pmol/mL) of antibacterial agents in Examples 1-13

| Sample No. | Strain | |
|---|---|---|
| | E. coli | S. aureas |
| Example 1 | 16 | 13 |
| Example 2 | 12 | 10 |
| Example 3 | 11 | 8 |
| Example 4 | 12 | 10 |
| Example 5 | 10 | 7 |
| Example 6 | 12 | 10 |
| Example 7 | 7 | 3 |
| Example 8 | 10 | 7 |
| Example 9 | 10 | 8 |
| Example 10 | 12 | 9 |
| Example 11 | 10 | 8 |
| Example 12 | 9 | 8 |
| Example 13 | 9 | 8 |

The compounds obtained in examples of the present disclosure have a quite low inhibitory concentration for the bacteria, which is sufficient to ensure that the number of bacterial populations is extremely low and do little harm to human health, when using the compounds.

Treating the clean glass surface with the products obtained in Examples 1-13 and the antibacterial activity and the durable antibacterial activity were tested using a colony counting method. The bacteria used in this implementation were *E. coli* and *S. aureas*, and the results are shown in Table 2.

TABLE 2

Durable antibacterial activity analysis for glass surfaces modified by antibacterial agents (plate counting method)

| Sample | Strain | Wash number | | | |
|---|---|---|---|---|---|
| | | 0 | 10 | 50 | 100 |
| Example 1 | E. coli | 99.99% | 99.8% | 97.5% | 96.0% |
| | S. aureas | 99.99% | 99.9% | 98.6% | 96.5% |
| Example 2 | E. coli | 99.99% | 99.9% | 97.3% | 95.9% |
| | S. aureas | 99.99% | 99.9% | 98.9% | 96.6% |
| Example 3 | E. coli | 99.99% | 99.8% | 98.5% | 96.5% |
| | S. aureas | 99.99% | 99.9% | 99.0% | 97.2% |
| Example 4 | E. coli | 99.99% | 99.8% | 98.0% | 94.2% |
| | S. aureas | 99.99% | 99.9% | 98.6% | 95.9% |

TABLE 2-continued

Durable antibacterial activity analysis for glass surfaces modified by antibacterial agents (plate counting method)

| Sample | Strain | Wash number 0 | 10 | 50 | 100 |
|---|---|---|---|---|---|
| Example 5 | E. coli | 99.99% | 99.7% | 99.0% | 96.5% |
|  | S. aureas | 99.99% | 99.9% | 99.5% | 98.5% |
| Example 6 | E. coli | 99.99% | 99.8% | 97.3% | 97.9% |
|  | S. aureas | 99.99% | 99.9% | 98.5% | 94.2% |
| Example 7 | E. coli | 99.99% | 99.92% | 99.9% | 95.2% |
|  | S. aureas | 99.99% | 99.95% | 99.9% | 95.2% |
| Example 8 | E. coli | 99.99% | 99.7% | 97.3% | 94.7% |
|  | S. aureas | 99.99% | 99.9% | 98.5% | 95.8% |
| Example 9 | E. coli | 99.99% | 99.8% | 97.1% | 94.3% |
|  | S. aureas | 99.99% | 99.9% | 98.5% | 95.2% |
| Example 10 | E. coli | 99.99% | 99.8% | 97.5% | 94.1% |
|  | S. aureas | 99.99% | 99.9% | 98.9% | 95.3% |
| Example 11 | E. coli | 99.99% | 99.8% | 97.1% | 94.5% |
|  | S. aureas | 99.99% | 99.9% | 98.3% | 95.8% |
| Example 12 | E. coli | 99.99% | 99.8% | 97.6% | 95.2% |
|  | S. aureas | 99.99% | 99.9% | 98.7% | 96.2% |
| Example 13 | E. coli | 99.99% | 99.8% | 97.5% | 95.3% |
|  | S. aureas | 99.99% | 99.9% | 98.8% | 96.5% |

According to the above table, the antibacterial compounds provided by the examples of the present disclosure have excellent antibacterial properties and durability against common bacteria such as *E. coli* and *S. aureas*. Even after repeated washing, the antibacterial properties only slightly reduced, but still remained at 94% or more.

The antibacterial compounds provided by the examples of the present disclosure have a reactive functional group—an isocyanate, which may chemically bond to the functional group present on the surfaces of a variety of materials, such as a hydroxyl in cotton fibers, fibrilia, polyester fibers (e.g., dacron PET), or poly lactic acid (PLA), an amino in nylon, as well as an amide in wool, pashm, silk, chinlon, or aramid, and anchor antibacterial components on the surfaces of materials, thus imparting durable soil resistance to the materials or product surfaces treated by the reactive antibacterial compounds. Meanwhile, the preparation method of the compound is simple, the condition is easy to control, and the compound is easy to be industrialized, which facilitate a wide use range of the compound. The antibacterial compounds provided by the examples of the present disclosure have broad industrial application prospects.

The foregoing is a further detailed description of embodiments of the present disclosure in conjunction with examples, which facilities those skilled in the art to readily understand and apply the antibacterial compounds provided by the embodiments of the present disclosure, and the embodiments of the present disclosure are not limiting. It should be noted that, without departing from the spirit of the embodiments of the present disclosure, other modifications or improvements may occur and are intended to those skilled in the art, and are within the scope of the present disclosure defined by the claims.

What is claimed is:

1. An antibacterial compound represented by formula (I):

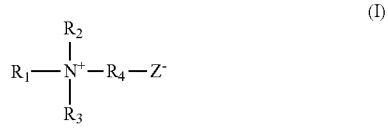

wherein:
R$_1$ represents OCN-L-NHCOOR', OCN-L-NHCONHR', OCN-L-NHCOSR', OCN-L-COOR', or OCN-L-COONHR';
L represents a divalent unsubstituted or substituted alkyl, cycloalkyl, or aryl having from 1 to 18 carbon atoms;
R' represents a divalent unsubstituted or substituted alkyl, cycloalkyl, or aryl having from 1 to 18 carbon atoms;
R$_2$ and R$_3$ independently for each occurrence represent a monovalent unsubstituted or substituted alkyl, cycloalkyl, or aryl having from 1 to 18 carbon atoms;
R$_4$ represents a divalent unsubstituted or substituted alkyl, cycloalkyl, or aryl having from 1 to 18 carbon atoms;
Z represents —COO, —SO$_3$, or —OPO$_2$OR$_5$; and
R$_5$ represents a monovalent unsubstituted or substituted alkyl, cycloalkyl, or aryl having from 1 to 6 carbon atoms.

2. The antibacterial compound of claim 1, wherein the R$_2$ and the R$_3$ independently for each occurrence represent —(CH$_2$)$_u$CH$_3$, and u is an integer within a range from 0 to 17.

3. The antibacterial compound of claim 1, wherein the R$_4$ and the R' independently for each occurrence represent —(CH$_2$)$_n$—, and n is an integer within a range from 1 to 18.

4. The antibacterial compound of claim 1, wherein the R$_1$ represents OCN-L-NHCOOR' or OCN-L-NHCONHR'.

5. The antibacterial compound of claim 1, wherein the L represents:

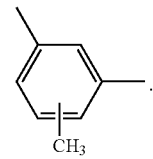

6. A preparation method for an antibacterial compound according to claim 1, comprising:
1) reacting tertiary amine represented by formula (III) with a reactant B represented by formula (IV), and generating a mixture;

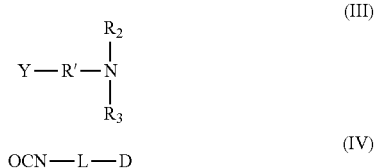

wherein:
the Y represents OH, —NH$_2$, or SH;
R' represents a divalent unsubstituted or substituted alkyl, cycloalkyl, or aryl having from 1 to 18 carbon atoms;
R$_2$ and R$_3$ independently for each occurrence represent a monovalent unsubstituted or substituted alkyl, cycloalkyl, or aryl having from 1 to 18 carbon atoms;
L represents a divalent unsubstituted or substituted alkyl, cycloalkyl, or aryl having from 1 to 18 carbon atoms; and
D represents —COOH or —NCO;
2) reacting the mixture with a reactant A, and generating the antibacterial compound represented by the formula (I);

wherein:
the reactant A represents propane sultone, butane sultone, β-propiolactone, $X(CH_2)_vCO_2$—$Mt^+$, $X(CH_2)_vSO_3$—$Mt^+$, or cyclic phosphate ester, the X represents Br, Cl, or I, v is an integer greater than 0, $Mt^+$ represents $Li^+$, $Na^+$, $K^+$, $NH_4+$, $Ag^+$, $\frac{1}{2}Mg^{2+}$, or $\frac{1}{2}Ca^{2+}$, and the cyclic phosphate ester represents:

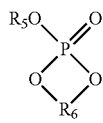

wherein:
$R_5$ represents a monovalent unsubstituted or substituted alkyl, cycloalkyl, or aryl having from 1 to 6 carbon atoms; and
$R_6$ represents a divalent unsubstituted or substituted alkyl having from 1 to 6 carbon atoms.

7. The preparation method for the antibacterial compound of claim 6, wherein the tertiary amine and the reactant B are reacting in the presence of catalyst C, and the catalyst C represents at least one of organic amine, a phosphorus compound, or a metal-containing catalyst.

8. The preparation method for the antibacterial compound of claim 7, wherein the metal-containing catalyst represents tin tetrachloride, tetrabutyl tin, tributyl tin chloride, dibutyl tin dichloride, butyl tin trichloride, tributyl tin cyanide, dibutyl tin diacetate, dibutyl tin dioctoate, tributyl tin octoate, diphenyl tin dioctoate, dibutyl tin dibutoxy, dibutyl tin bis(acetylacetoate), dibutyl tin bis(isooctylmaleate), dioctoate tin oxide, dibutyl tin sulfide, stannous oleate, stannous tartrate, dibutyl tin dilaurate, stannous octoate, or metal naphthenate.

9. The preparation method for the antibacterial compound of claim 8, wherein the catalyst C represents the metal naphthenate.

10. The preparation method for the antibacterial compound of claim 9, wherein the metal naphthenate represents at least one of copper naphthenate, zinc naphthenate, lead naphthenate, lithium naphthenate, cobalt naphthenate, nickel naphthenate, cadmium naphthenate, mercury naphthenate, indium naphthenate, or bismuth naphthenate.

11. An antibacterial compound represented by formula (I):

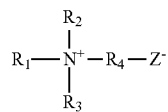

(I)

wherein:
$R_1$ represents OCN-L-NHCOOR' or OCN-L-NHCONHR';
L represents a divalent unsubstituted or substituted alkyl, cycloalkyl, or aryl having from 1 to 18 carbon atoms;
R' represents a divalent unsubstituted or substituted alkyl, cycloalkyl, or aryl having from 1 to 18 carbon atoms;
$R_2$ and $R_3$ independently for each occurrence represent a monovalent unsubstituted or substituted alkyl, cycloalkyl, or aryl having from 1 to 18 carbon atoms;

$R_4$ represents a divalent unsubstituted or substituted alkyl, cycloalkyl, or aryl having from 1 to 18 carbon atoms;
Z represents —COO, —$SO_3$, or —$OPO_2OR_5$; and
$R_5$ represents a monovalent unsubstituted or substituted alkyl, cycloalkyl, or aryl having from 1 to 6 carbon atoms.

12. The antibacterial compound of claim 11, wherein the $R_4$ and the R' independently for each occurrence represent —$(CH_2)_n$—, and n is an integer within a range from 1 to 18.

13. The antibacterial compound of claim 11, wherein the L represents:

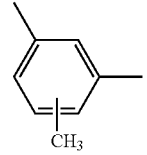

14. A preparation method for an antibacterial compound according to claim 11, comprising:
1) reacting tertiary amine represented by formula (III) with a reactant B represented by formula (IV), and generating a mixture;

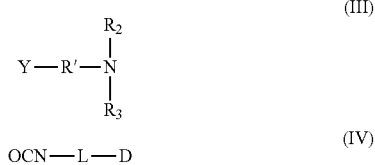

wherein:
the Y represents —OH, —$NH_2$, or —SH;
R' represents a divalent unsubstituted or substituted alkyl, cycloalkyl, or aryl having from 1 to 18 carbon atoms;
$R_2$ and $R_3$ independently for each occurrence represent a monovalent unsubstituted or substituted alkyl, cycloalkyl, or aryl having from 1 to 18 carbon atoms;
L represents a divalent unsubstituted or substituted alkyl, cycloalkyl, or aryl having from 1 to 18 carbon atoms; and
D represents —COOH or —NCO;
2) reacting the mixture with a reactant A, and generating the antibacterial compound represented by the formula (I);
wherein:
the reactant A represents propane sultone, butane sultone, β-propiolactone, $X(CH_2)_vCO_2$—$Mt^+$, $X(CH_2)_vSO_3$—$Mt^+$, or cyclic phosphate ester, the X represents Br, Cl, or I, v is an integer greater than 0, $Mt^+$ represents $Li^+$, $Na^+$, $K^+$, $NH_4^+$, $Ag^+$, $\frac{1}{2}Mg^{2+}$, or $\frac{1}{2}Ca^{2+}$, and the cyclic phosphate ester represents:

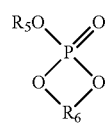

wherein:
$R_5$ represents a monovalent unsubstituted or substituted alkyl, cycloalkyl, or aryl having from 1 to 6 carbon atoms; and $R_6$ represents a divalent unsubstituted or substituted alkyl having from 1 to 6 carbon atoms.

15. The preparation method for the antibacterial compound of claim 14, wherein the tertiary amine and the reactant B are reacting in the presence of catalyst C, and the catalyst C represents at least one of organic amine, a phosphorus compound, or a metal-containing catalyst.

16. The preparation method for the antibacterial compound of claim 15, wherein the metal-containing catalyst represents tin tetrachloride, tetrabutyl tin, tributyl tin chloride, dibutyl tin dichloride, butyl tin trichloride, tributyl tin cyanide, dibutyl tin diacetate, dibutyl tin dioctoate, tributyl tin octoate, diphenyl tin dioctoate, dibutyl tin dibutoxy, dibutyl tin bis(acetylacetoate), dibutyl tin bis(isooctyl-maleate), dioctoate tin oxide, dibutyl tin sulfide, stannous oleate, stannous tartrate, dibutyl tin dilaurate, stannous octoate, or metal naphthenate.

17. The preparation method for the antibacterial compound of claim 16, wherein the catalyst C represents the metal naphthenate.

18. The preparation method for the antibacterial compound of claim 17, wherein the metal naphthenate represents at least one of copper naphthenate, zinc naphthenate, lead naphthenate, lithium naphthenate, cobalt naphthenate, nickel naphthenate, cadmium naphthenate, mercury naphthenate, indium naphthenate, or bismuth naphthenate.

19. An antibacterial compound selected from a group consists of

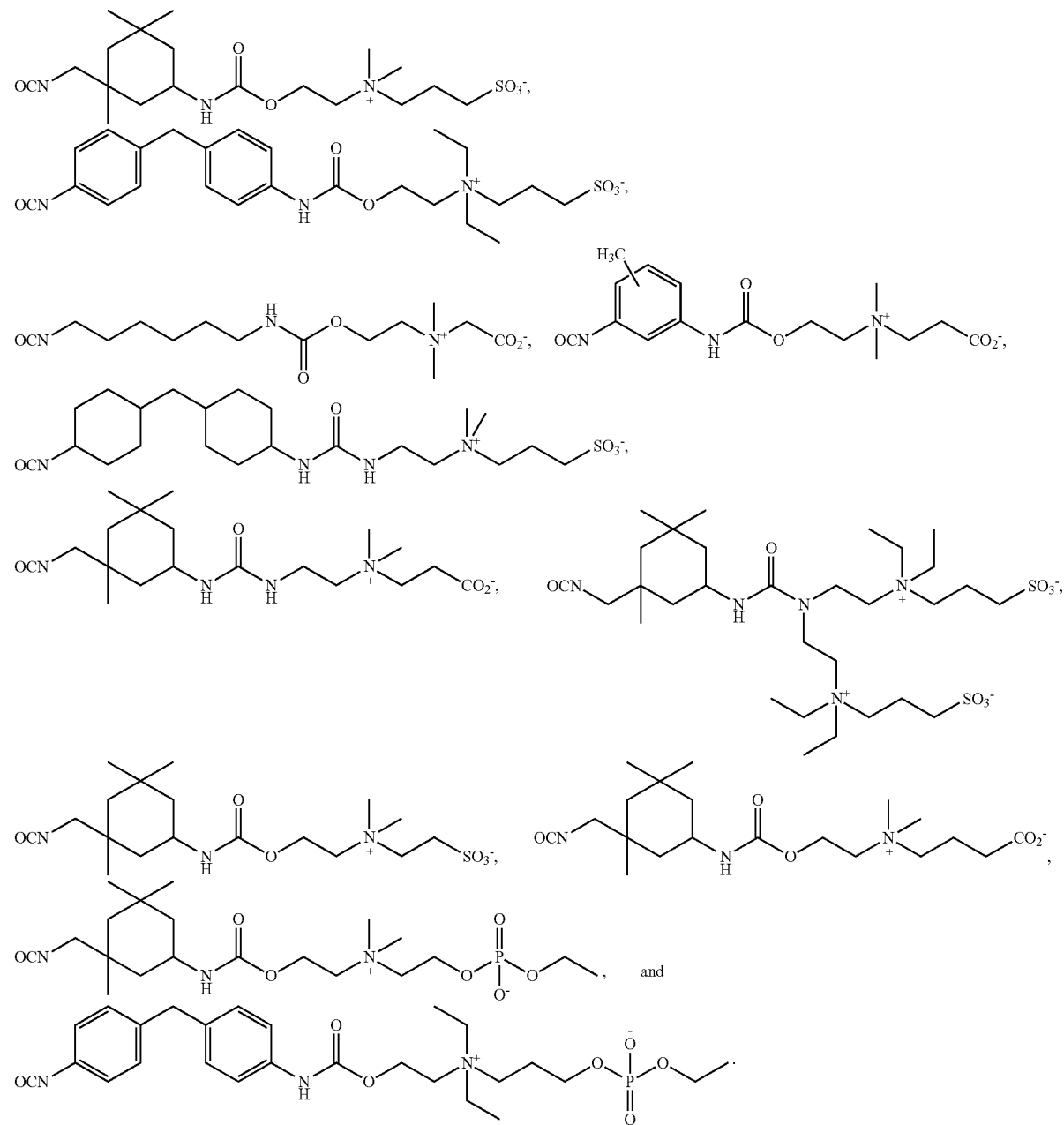

20. A preparation method for an antibacterial compound according to claim 19, comprising:

1) reacting tertiary amine represented by formula (III) with a reactant B represented by formula (IV), and generating a mixture;

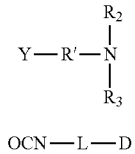
(III)

OCN—L—D (IV)

wherein:
the Y represents —OH, —NH$_2$, or —SH;
R' represents a divalent unsubstituted or substituted alkyl, cycloalkyl, or aryl having from 1 to 18 carbon atoms;
R$_2$ and R$_3$ independently for each occurrence represent a monovalent unsubstituted or substituted alkyl, cycloalkyl, or aryl having from 1 to 18 carbon atoms;
L represents a divalent unsubstituted or substituted alkyl, cycloalkyl, or aryl having from 1 to 18 carbon atoms; and
D represents —COOH or —NCO;
2) reacting the mixture with a reactant A, and generating the antibacterial compound;
wherein:
the reactant A represents propane sultone, β-propiolactone, ClCH$_2$CO$_2$Na, BrCH$_2$CH$_2$SO$_3$Na, BrCH$_2$CH$_2$CH$_2$CO$_2$Na, 2-ethoxy-2-oxy-1,3,2-dioxaphospholane (EOP), or 2-ethoxy-2-oxy-1,3,2-dioxaphosphinan,
the tertiary amine and the reactant B are reacting in the presence of catalyst C, and the catalyst C represents at least one of organic amine and a metal-containing catalyst, and
the metal-containing catalyst represents dibutyl tin dilaurate or stannous octanoate.

* * * * *